(12) United States Patent
McArthur et al.

(10) Patent No.: US 6,719,017 B1
(45) Date of Patent: Apr. 13, 2004

(54) WASTE COLLECTION SYSTEM FOR CONTAINMENT AND DISPOSAL OF CONTAMINATED FLUIDS

(75) Inventors: Greg McArthur, Sandy, UT (US); Fred P. Lampropoulos, Sandy, UT (US); Arlin D. Nelson, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 10/043,549

(22) Filed: Jan. 10, 2002

(51) Int. Cl.[7] .................................. F23G 5/12
(52) U.S. Cl. ..................... 141/86; 141/311 A; 141/98; 141/110; 206/366; 604/110; 604/192
(58) Field of Search ................. 141/86, 88, 311 A, 141/98, 110; 137/312; 206/366, 370; 604/110, 192

(56) References Cited

U.S. PATENT DOCUMENTS

| | | |
|---|---|---|
| 3,215,299 A | 11/1965 | Coanda et al. |
| 3,387,732 A | 6/1968 | Jellies |
| 3,537,498 A | 11/1970 | Amand |
| 3,581,928 A | 6/1971 | Amand |
| 3,635,367 A | 1/1972 | Morita et al. |
| 3,901,399 A | 8/1975 | McPhee |
| 4,088,166 A | 5/1978 | Miller |
| 4,090,541 A | 5/1978 | Cammarata, III et al. |
| 4,199,062 A | 4/1980 | Johnston et al. |
| 4,232,721 A | 11/1980 | Martin et al. |
| 4,274,848 A * | 6/1981 | La Gro ............................. 96/6 |
| 4,301,935 A | 11/1981 | Gokeen et al. |
| 4,308,904 A | 1/1982 | Martin et al. |
| 4,465,487 A | 8/1984 | Nakamura et al. |
| 4,488,643 A | 12/1984 | Pepper |
| 4,581,763 A | 4/1986 | Olsen |
| 4,615,045 A | 9/1986 | Siegel |
| 4,641,680 A | 2/1987 | Been |
| 4,672,688 A | 6/1987 | Kalkipsakis |
| 4,728,504 A | 3/1988 | Nichols |
| 4,845,487 A | 7/1989 | Frantz et al. |
| 4,850,807 A | 7/1989 | Frantz |
| 4,874,103 A | 10/1989 | Quisenberry et al. |
| 4,940,157 A | 7/1990 | Inagaki |
| 4,946,290 A | 8/1990 | Matyja |
| 4,953,708 A | 9/1990 | Beer et al. |
| 4,991,731 A | 2/1991 | Osip et al. |
| 5,023,119 A | 6/1991 | Yamakoshi |
| 5,039,004 A | 8/1991 | Simpson |
| 5,083,678 A | 1/1992 | Waring |
| 5,100,000 A | 3/1992 | Huseman |
| 5,116,139 A | 5/1992 | Young et al. |
| D330,417 S | 10/1992 | Bell |
| 5,152,394 A | 10/1992 | Hughes |
| 5,163,375 A | 11/1992 | Withers et al. |
| 5,167,193 A | 12/1992 | Withers et al. |
| 5,172,808 A | 12/1992 | Bruno |
| 5,259,501 A | 11/1993 | Withers et al. |
| 5,265,724 A | 11/1993 | Dondlinger |
| 5,483,999 A | 1/1996 | Lampropoulos et al. |
| 5,707,173 A | 1/1998 | Cottone et al. |
| 6,053,314 A | 4/2000 | Pittman |

FOREIGN PATENT DOCUMENTS

GB 2 251 423 A 7/1992

* cited by examiner

Primary Examiner—Gregory Huson
Assistant Examiner—Peter deVore
(74) Attorney, Agent, or Firm—TraskBritt

(57) ABSTRACT

The present invention provides a waste collection system including a receptacle housing at least one chamber configured to accept waste and at least one containment layer configured to retain waste within the at least one chamber. The at least one chamber of the at least one containment layer includes a vent to allow gases to escape from the chamber. The at least one containment layer may be configured to quickly deliver waste to an aperture therein. A valve member configured to direct waste into the at least one chamber may be associated with the aperture. A method of using the waste collection system is also provided.

70 Claims, 16 Drawing Sheets

WASTE COLLECTION SYSTEM FOR CONTAINMENT AND DISPOSAL OF CONTAMINATED FLUIDS

BACKGROUND OF THE INVENTION

1. Field of the Invention

The present invention relates to waste collection systems. More particularly, the present invention relates to waste collection systems for receiving contaminated fluids in a manner which reduces splashing or spilling.

2. State of the Art

The collection, containment, and disposal of contaminated fluids are becoming increasing concerns with respect to environmental protection and the protection of persons involved in handling such fluids. Perhaps nowhere is the concern greater than in the context of handling and disposing of contaminated physiological fluids. For example, physiological fluids must be handled, collected, contained, and then disposed of on a daily basis in catheter labs.

In many catheter lab procedures it is common to have a table set up in the back of the lab which is often referred to as the "back table." This table is used for setting up many types of medical instruments, and their associated couplings, to intravenous tubing and the like. The back table is also commonly used for collection and disposal of contaminated physiological fluids, both during and after a particular procedure has been performed.

For example, during angiography and angioplasty procedures, a great deal of blood and other fluids that may have been administered intravenously are accumulated. Numerous procedures involve the injection of fluids or other substances into the body for evaluation by x-ray or other imaging. Fluids may be transferred to or from the body via needle-type syringes and into intravenous lines via blunt-tip syringes that must be drained before disposal. Doctors and medical personnel need a convenient and rapid system for collecting and disposing fluids, especially due to the growing risk to health care personnel who may come in contact with blood or other physiological fluids that may have become contaminated with the HIV (AIDS) virus, hepatitis, or other communicable diseases. Thus, the health care industry is constantly looking for ways to improve the working environment by minimizing the possibility of contacting contaminated fluids.

Traditionally, catheter labs used products such as vinyl film bags with tubing lines that require attachment of a manifold or syringe for the collection of blood and other fluids procedures. Other catheter labs simply use open basins to collect waste or let the contaminated fluid waste collect on an absorbent towel. Such procedures and methods for collecting and disposing contaminated fluids are inadequate. Use of the vinyl film bags is often overly complicated and time consuming and requires the interconnection of various components. Such products are also unduly complicated and costly. When open basins or absorbent towels are used, personnel are not adequately protected against splash, spillage, and the like. Another example of a product used in catheter labs is the receptacle described by U.S. Pat. No. 6,053,314 to Pittman. However, the Pittman receptacle uses fibrous absorptive material that often contacts and thus contaminates the syringe used to deliver fluids to the receptacle. Further, the Pittman receptacle does not sufficiently retain waste within the receptacle.

One product that overcomes the shortcomings in the prior art is the waste collection system described in U.S. Pat. No. 5,483,999 to Lampropoulos et al., assigned to the assignee herein, the disclosure of which is incorporated herein by reference. FIG. 1 illustrates one aspect of the Lampropoulos et al. waste collection system 100' including a receptacle 20' housing an absorbent layer 24', a first containment layer 22' and a second containment layer 34'. The first containment layer 22' is shown having a plurality of channels 38' which slope downward toward a central opening 40'. A valve member 42' rests over the central opening 40' such that any fluid in the channels 38' must pass through the valve member 42' to enter the receptacle 20'. However, fluid may contain viscous material which may be trapped in the channels 38' against the valve member 42' and may prevent additional fluid from passing through the valve member 42' and into the receptacle 20'. Further, the valve member 42' may create a lock wherein pressure below the valve member 42' is too high and fluid pools on top of the first containment layer 22', which creates safety problems for personnel. Further, the illustrated embodiment does not provide an easily accessible portion for collecting particulate waste or storing objects that may be associated with the collection and disposal of contaminated fluids. Additionally, the preferred embodiment is not large enough to accommodate fluid collected during many procedures.

Thus, it would be desirable to provide a container for handling and disposing fluids that would more easily accommodate storage and both fluid and particulate waste. Additionally, it would be desirable to design a waste collection system for improved drainage for fluids having viscous matter. Further, it would be desirable to provide a waste collection system configured to minimize a syringe, or other fluid delivery vessel, from becoming contaminated during collection of fluids.

BRIEF SUMMARY OF THE INVENTION

One aspect of the present invention provides a waste collection system including a receptacle housing having at least one chamber configured to accept waste. The receptacle may include at least a first chamber configured to accept fluid waste and at least a second chamber configured to accept particulate waste or to serve as a storage compartment. The waste collection system may further include at least one containment layer, lid or insert configured to retain waste within the at least one chamber. Alternatively, the at least one containment layer may be configured to retain waste within the multi-chambered receptacle.

At least one chamber may include at least one vent. The vent may be an S-shaped or L-shaped recess in a portion of an at least one containment layer or a recessed portion of a sidewall of the at least one chamber or a portion of the at least one containment layer. When an at least one containment layer is used with the receptacle, the vent allows fluids to drain more quickly into the receptacle by allowing gases to escape from a covered receptacle.

At least one containment layer may be configured to assist in the collection of fluid waste. In this embodiment, the at least one containment layer includes a plurality of surfaces sloping toward at least one opening therein. A plurality of channels may be formed between the plurality of sloping surfaces and may be configured to deliver waste into the at least one opening. The opening may be circular, funnel-shaped or frusto-conical. In one embodiment, the at least one containment layer further includes a hood partially covering the at least one opening. Further, in one embodiment, the at least one containment layer and receptacle are formed as a unitary member.

The waste collection system may further include a valve member positioned adjacent the at least one opening. The valve member may be configured to accept and retain waste below the at least one containment layer and may have characteristics of a valve, baffle, dam and the like. The valve member may be a funnel-shaped member or a circular disc and formed from foam, rubber or plastic. In one embodiment, the valve member includes a plurality of flaps extending from the at least one containment layer and surrounding a central aperture.

The valve member may rest on a ledge surrounding the at least one opening and between each channel such that a gap is formed between the valve member and the plurality of channels. This design may allow waste to enter the at least one opening through the gap rather than through the valve member.

The at least one containment layer may cover the entire multi-chambered receptacle as well as accept a second receptacle of a second waste collection system. The receptacle may include a plurality of sidewalls with at least one sidewall including at least one detent. In this embodiment, the at least one containment layer may include at least one pocket for accepting the at least one detent so that the at least one containment layer may accept and stabilize the receptacle during waste collection.

The waste collection system may further include at least one absorbent layer within at least one chamber. The absorbent layer may be at least one of wood pulp filler, super-absorbent polymer filler, and water-based guar gel.

In another aspect of the present invention, a waste collection system is provided including a basin including at least one chamber configured to receive fluids. A second chamber that is configured to receive particulate waste or to serve as a storage compartment may be provided. A first containment layer at least partially covers the at least one chamber and includes at least one aperture for receiving waste. A vent is associated with either the at least one chamber or the first containment layer.

In yet another aspect of the present invention, a lid for use with a waste collection system is provided. The lid may include a plurality of surfaces sloping toward at least one aperture therein. At least one channel may be formed between the plurality of sloping surfaces. A valve member may be positioned adjacent the at least one aperture such that a gap is formed beneath the valve member and above the at least one channel.

The lid may be used in combination with a receptacle to deliver fluid waste into the receptacle with a decreased risk that the fluid will splash or spill out of the receptacle. The valve member may be configured to accept and retain fluids beneath the lid.

An improved method of collecting fluid waste is also provided. The method includes providing a receptacle including at least one chamber configured to accept fluid waste, at least one vent and at least one containment layer. Fluid waste is delivered to the receptacle and gases within the receptacle are allowed to escape through the vent. The vent may comprise an S-shaped or L-shaped recess in a portion of an at least one containment layer, or a recessed portion of a sidewall of at least one chamber or a portion of an at least one containment layer. At least one absorbent layer may be placed within the at least one chamber.

Fluid waste may be delivered to the receptacle in several ways. Fluid waste may be introduced to a surface of the at least one containment layer and allowed to flow into an aperture within the at least one containment layer. The fluid waste may flow between the surface and a valve member positioned adjacent the aperture. Fluid waste may be delivered by introducing the fluid waste directly into an aperture in the at least one containment layer. Fluid waste may be delivered by penetrating a valve member positioned adjacent an aperture in the at least one containment layer. For example, a syringe may be used to penetrate a valve member and release fluid into the receptacle.

The method may further include attaching a base of the receptacle and the at least one containment layer so as to stabilize the receptacle while delivering the fluid waste. The at least one containment layer may be removed from the base of the receptacle and reattached to the top of the receptacle to cover the receptacle. A base of a receptacle of a second waste collection system may then be placed on the at least one containment layer.

BRIEF DESCRIPTION OF THE SEVERAL VIEWS OF THE DRAWINGS

The foregoing and other advantages of the invention will become apparent upon reading the following detailed description and upon reference to the drawings in which:

FIG. 19b is a side view of the unitary receptacle and at least one containment layer of a waste collection system of the present invention shown in FIG. 19a.

DETAILED DESCRIPTION OF THE INVENTION

Figure 1:
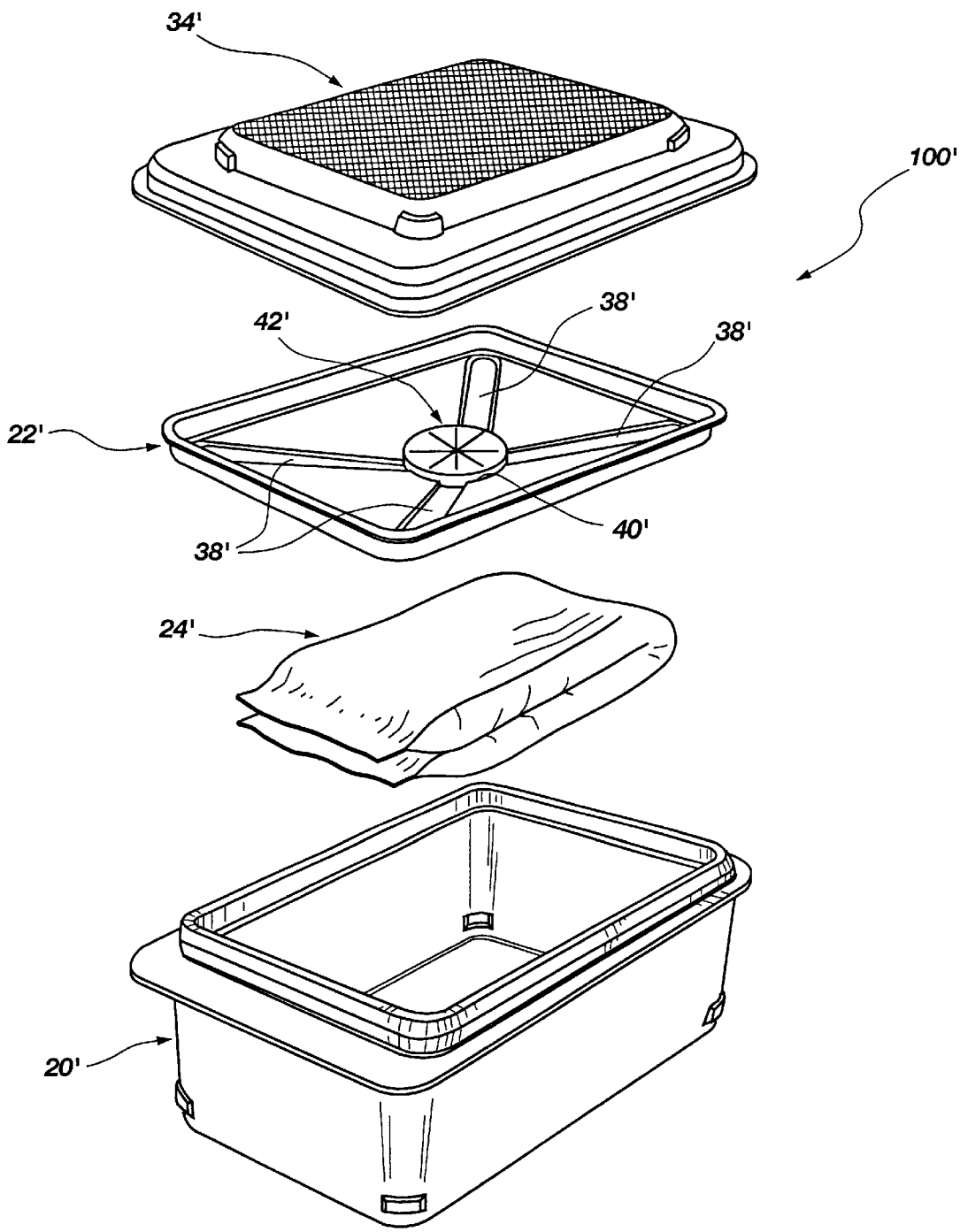
FIG. 1 illustrates an exploded perspective view of a prior art embodiment of a waste collection system.
Figure 2:
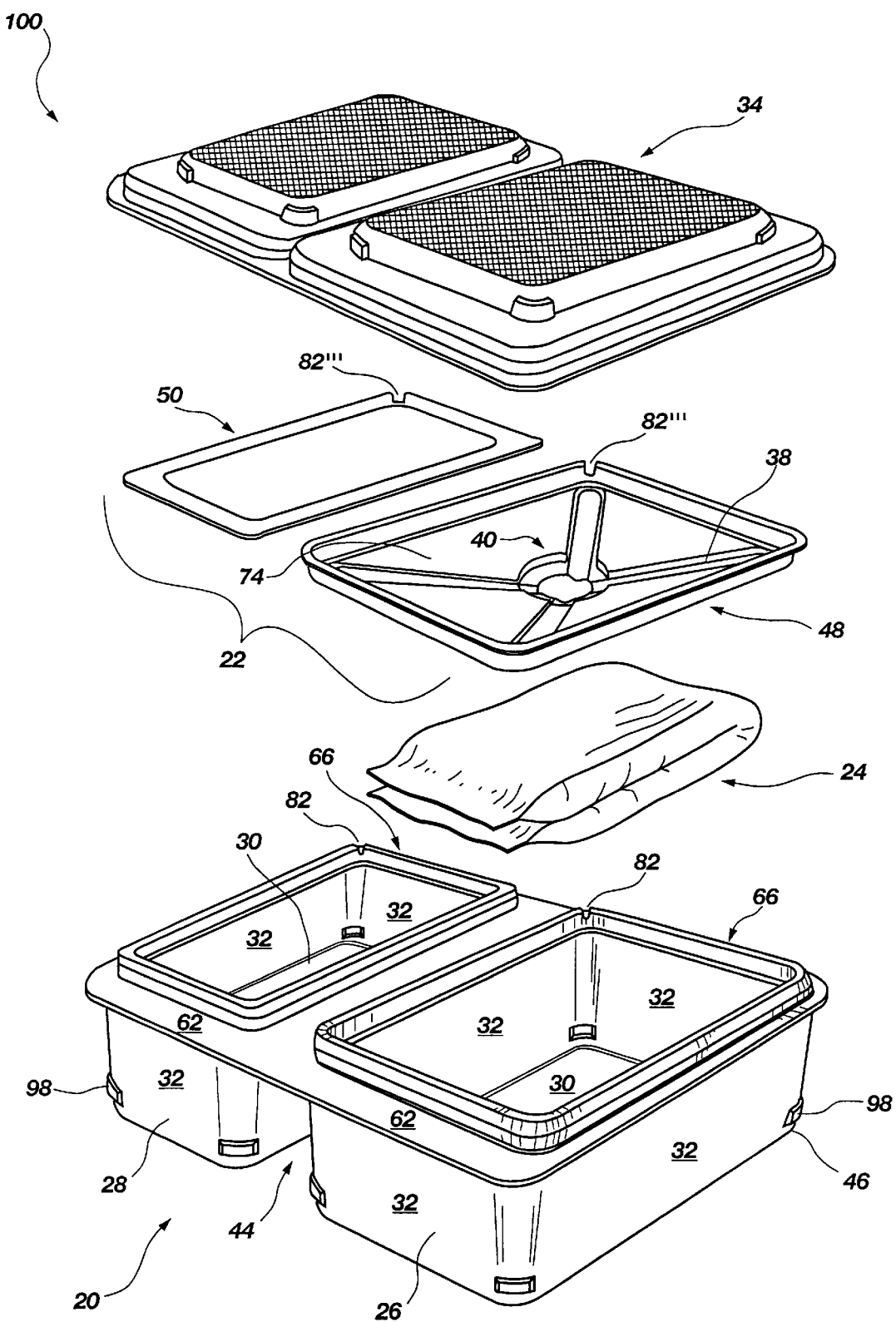
FIG. 2 illustrates an exploded perspective view of one embodiment of a waste collection system of the present invention.

Elements common throughout the drawings retain the same numeric designation herein. FIG. 2 illustrates an exploded view of one embodiment of a waste collection system 100 of the present invention including a receptacle or basin 20 and an optional combination of components including an absorbent layer 24, first containment layer 22 (shown as including a first segment 48 and a second segment 50) and second containment layer 34. FIG. 2 depicts an embodiment of the present invention wherein the receptacle 20 includes a substantially rectangular body. However, the receptacle 20 may be square, triangular, pyramidal, circular, oval or any other desired shape. In one aspect of the present invention, the receptacle 20 includes a first chamber 26 and a second chamber 28; however, any desired number of chambers may be included within the receptacle 20. Additionally, while FIG. 2 depicts the first chamber 26 as being larger than a second chamber 28, it may be desirable to have two equal-sized chambers or a combination of multi-sized chambers. In one embodiment, the receptacle 20 may include a space 44 between the first chamber 26 and second chamber 28.

The receptacle 20 may be formed of any substantially rigid, leak-proof material that will contain fluids, including contaminated fluids. In one embodiment, the receptacle 20 may be formed as a molded, unitary plastic member. The receptacle 20 may also be formed of styrene, fiberboard, laminated or lined cardboard, molded cellulose, paper stock, wood and particle board, rayon, cellophane, cellulose-nitrate, rubber, wax, or any lightweight metal material.

The first chamber 26 and second chamber 28 may each include a bottom 30, four sidewalls 32 and an open top. The four sidewalls 32 may be any desired height sufficient to contain fluid or other matter therein. It is contemplated that at least one chamber within the receptacle 20 may be configured to accept fluids. Thus, in one embodiment, the four sidewalls 32 may be a sufficient height to contain a desired volume of fluid. Further, the four sidewalls 32 may be of a sufficient height such that when a syringe, or other fluid delivery device, is inserted through an opening 40 in a first containment layer 22, the syringe will not readily contact either the bottom 30 of a chamber of the receptacle 20 or any absorbent layer 24 therein. If more than one chamber is provided within the receptacle 20, it is contemplated that at least one chamber may be configured to accept particulate waste, such as, for example, paper waste, sponges, etc. Further, the at least one chamber may be used as a storage compartment. Depending upon the construction material used, the sidewalls 32 of the chambers 26, 28 of receptacle 20 may include ribs or other structures for added support and reinforcement (not shown).

In one embodiment, the corners 46 where the sidewalls 32 and the bottom 30 meet are slightly rounded to increase the volume capacity of the chamber and to stabilize the waste collection system 100. The bottom 30 of each chamber 26, 28 may be slightly smaller than the open top and the sidewalls 32 may slope downward toward the bottom 30. Alternatively, the bottom 30 may be approximately the same size or slightly larger than the open top for added stability. The four sidewalls 32 may also include external detents 98 as further described herein.

A snap ring 66 may be formed around each of the first chamber 26 and the second chamber 28 and may be molded as a continuous part of the sidewalls 32 in one embodiment. Alternatively, a snap ring may be formed around the entire perimeter of the receptacle (not shown). The snap ring 66 engages with the first containment layer 22 and/or second containment layer 34. The snap ring 66 may include a horizontal rim or shelf 62 that extends around the entire periphery of receptacle 20 or around each chamber 26, 28 therein.

The waste collection system 100 may also include a first containment layer 22 that retains fluids or other contents of the receptacle 20 therein. In one embodiment, the first containment layer 22 may be transparent. The first containment layer 22 may include a first segment 48 configured to cover a first chamber 26 and a second segment 50 configured to cover a second chamber 28. While FIG. 2 illustrates the first containment layer 22 as having two separate segments, it will be understood that the first containment layer 22 may include a sufficient number of segments to cover all chambers within a receptacle 20.

At least a first segment 48 of the first containment layer 22 may include downward-sloping surfaces 74 and a plurality of channels 38 that meet at an opening or aperture 40 such that the first segment 48 functions as a large funnel, directing fluid on the sloping surfaces and in the plurality of channels 38 into the opening 40. While FIG. 2 illustrates four channels 38, any desired number of channels may be used. An opening 40 may be centrally located; however, the opening 40 may be located in any desired location. Alternatively, the opening 40 may be located within the receptacle 20.

In prior art waste collection systems, fluids would often pool above a receptacle opening because of air being trapped within the receptacle. Thus, in one embodiment, the receptacle 20 may include a vent 82 which may be formed as part of at least one chamber within the receptacle 20. The vent 82 allows air or other gases to escape from the receptacle 20 when the first containment layer 22 is attached thereto. Thus, the vent 82 aids in increasing the rate of flow of fluid on the first containment layer 22 into the receptacle 20 by allowing air or any atmosphere within the enclosed receptacle 20 to be vented. The segments 48, 50 of the first containment layer 22 may also include a vent 82'''.

In another aspect of the present invention, at least one absorbent layer 24 may be included within the receptacle 20. The absorbent layer 24 may collect and hold fluid within the receptacle 20. The absorbent layer 24 may be folded to form two layers such that an upper layer may be positioned directly beneath the opening 40 so that fluid which enters through the opening 40 may be readily absorbed and retained by the upper layer. Any fluid that reaches the bottom 30 of a chamber of the receptacle 20 may be readily absorbed and retained by the lower layer.

The absorbent layer 24 may comprise any absorbent material that will not leave particulate matter on the fluid delivery device (such as a syringe) if accidentally contacted during delivery of fluid. For example, the absorbent layer 24 may include a diaper-type pad which may be doubled and which may be comprised of a cotton top sheet with wood pulp filler and a super-absorbent polymer filler enclosed within the cotton top sheet. The absorbent layer 24 may also be optionally treated with a disinfectant such as a suitable disinfectant for killing the HIV (AIDS) virus, hepatitis, or other types of communicable viruses or bacteria. The absorbent layer 24 may also comprise a water-based (hydrophilic) guar gel as known in the art. The absorbent layer 24 may gel very rapidly upon contact with a water-based liquid and which by gelling completely absorbs and encapsulates fluid therein.

In still a further aspect of the present invention, the waste collection system 100 may further comprise a second containment layer 34 which may be used for both supporting and stabilizing the receptacle 20 on a surface while waste is collected in the receptacle 20 (not shown in FIG. 2) and enclosing the receptacle 20 and first containment layer 22 to help retain fluid or any other waste in the receptacle 20 ready for disposal after it is collected. The second containment layer 34 may be formed as a unitary piece of molded plastic material. The second containment layer 34 may attach to the bottom 30 of the chambers of receptacle 20 (not shown in FIG. 2) during stabilization and waste collection and may be removed from the bottom 30 and placed on top of the receptacle 20 after waste collection.

Figure 3:
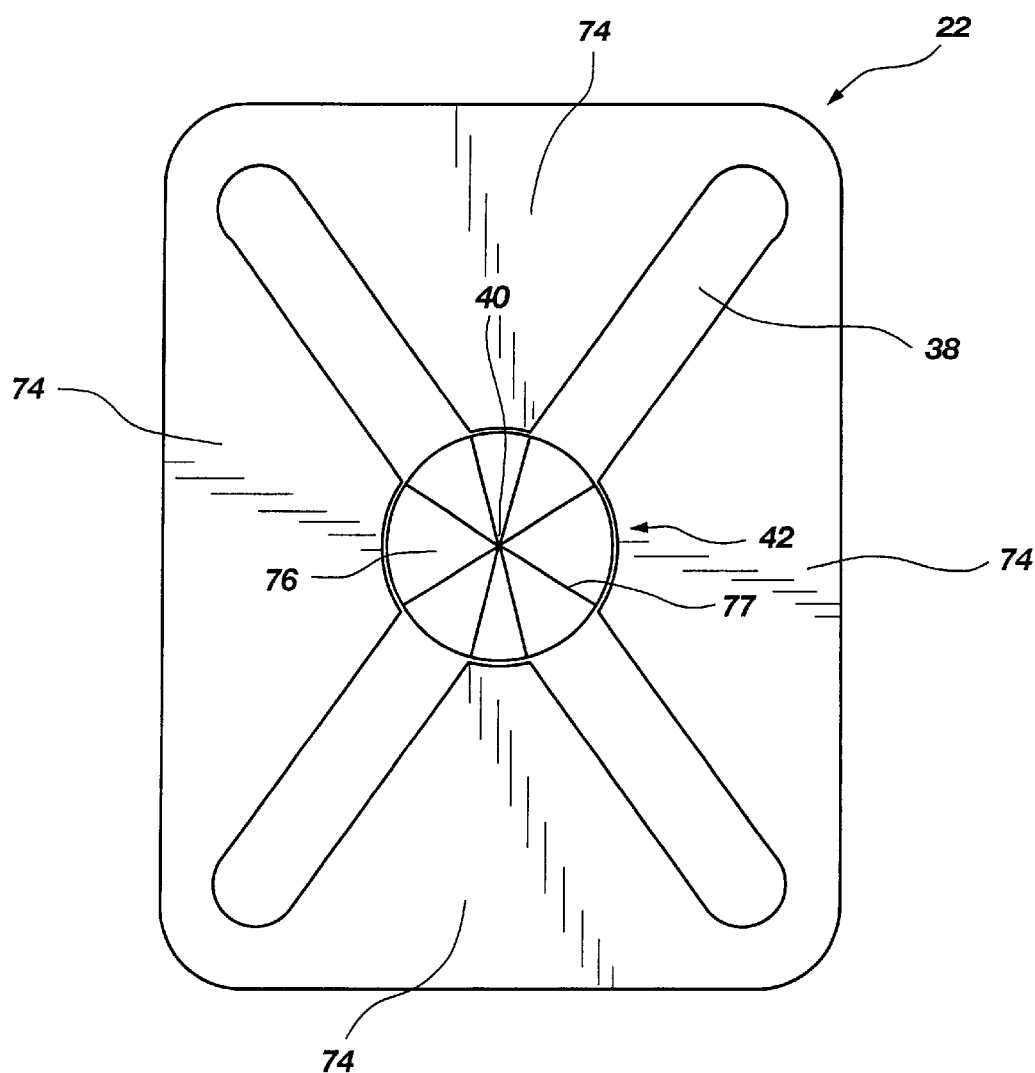
FIG. 3 illustrates a top view of one embodiment of an at least one containment layer of a waste collection system of the present invention.

FIG. 3 illustrates an alternate embodiment of the invention wherein the first containment layer 22 includes a valve member 42. Alternatively, the valve member 42 may be disposed on the receptacle 20 (not shown). The valve member 42 allows fluids to enter the receptacle 20 through an opening 40 and contains fluids thereunder, decreasing splashing or spilling, and may have characteristics of a valve, baffle, dam and the like. Thus, fluids on the surfaces 74 or in the channels 38 of the first containment layer 22 may pass through the valve member 42 before entering the receptacle 20. The valve member 42 may include a plurality of slits 77 that form a plurality of flaps 76 around a central aperture. Thus, a fluid delivery device, such as a syringe, may penetrate valve member 42 and deliver fluid to the receptacle 20 while the flaps 76 minimize fluid splashing above the opening 40.

The valve member 42 may comprise a circular disc that may be placed above the opening 40 formed near the center of first containment layer 22. The circular disc may be formed from foam material that provides absorption and wicking action for fluids contacting the foam material, such that fluids will readily pass through the foam material with decreased splashing and without beading up. One example of the foam material is a natural die-cut foam of a type which is specified as 100 ppi SIF "z," manufactured and sold by Aspen Sales, 5258 Pinemont Drive, Suite B-200, Murray, Utah, 84123. Alternatively, the valve member 42 may be rubber, plastic, metal, or porous (such as a sponge or other absorbent material). Thus, the valve member 42 accepts fluids and retains the fluids below the first containment layer 22.

Figure 4A:
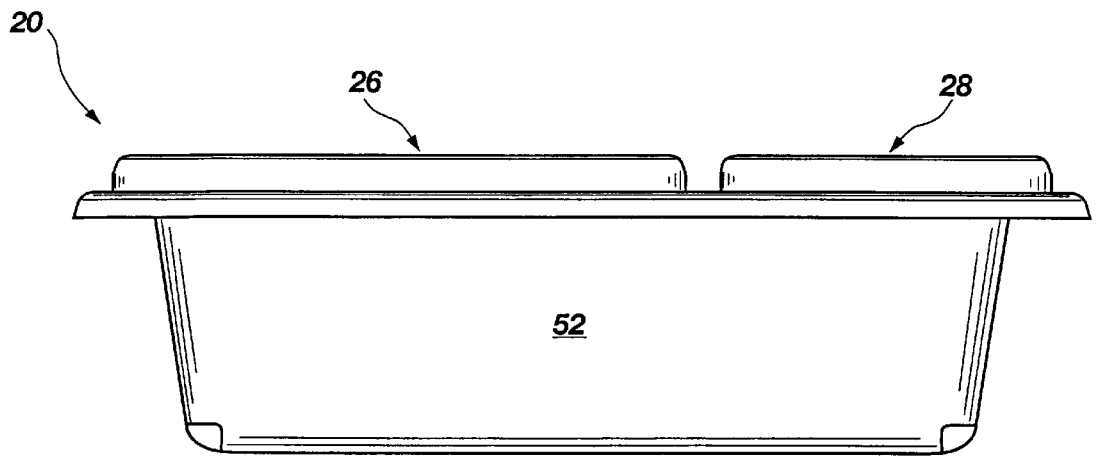
FIG. 4a is a side view of one embodiment of a receptacle of a waste collection system of the present invention.
Figure 4B:
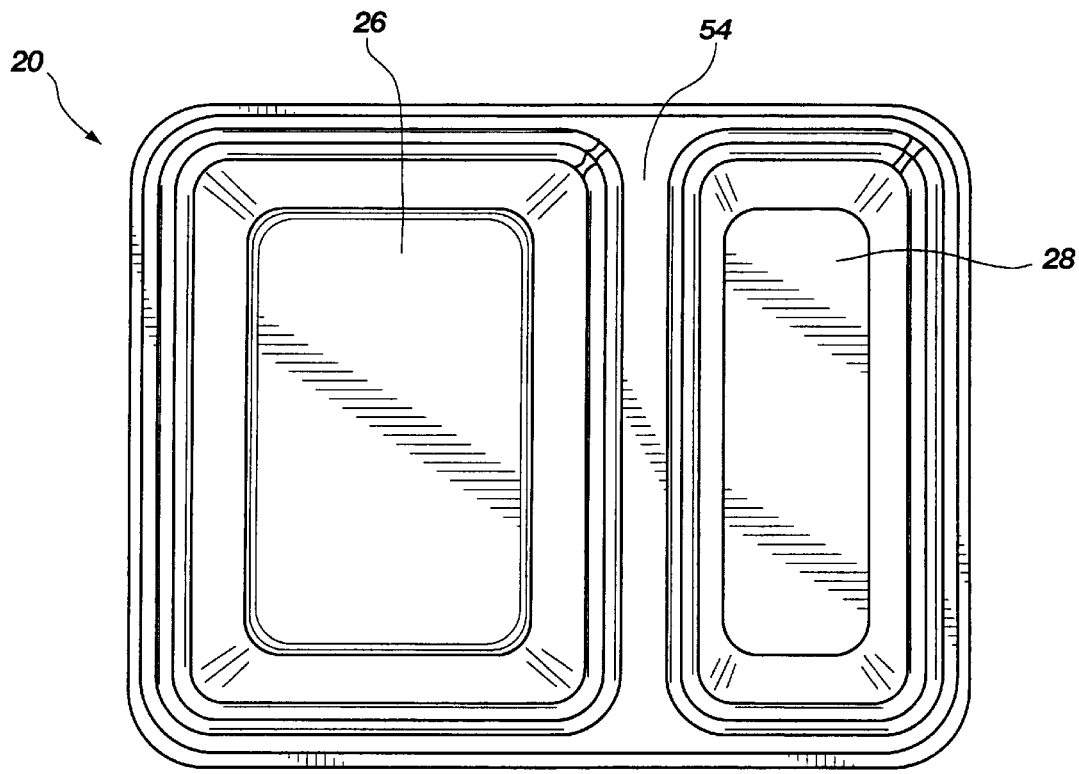
FIG. 4b is a top view of one embodiment of a receptacle of a waste collection system of the present invention.

FIG. 4a and FIG. 4b depict another embodiment of the present invention wherein the receptacle 20 may be configured having a continuous wall 52 around the perimeter of the first chamber 26 and second chamber 28 and a dividing wall 54 that separates the first chamber 26 from the second chamber 28.

Figure 5:
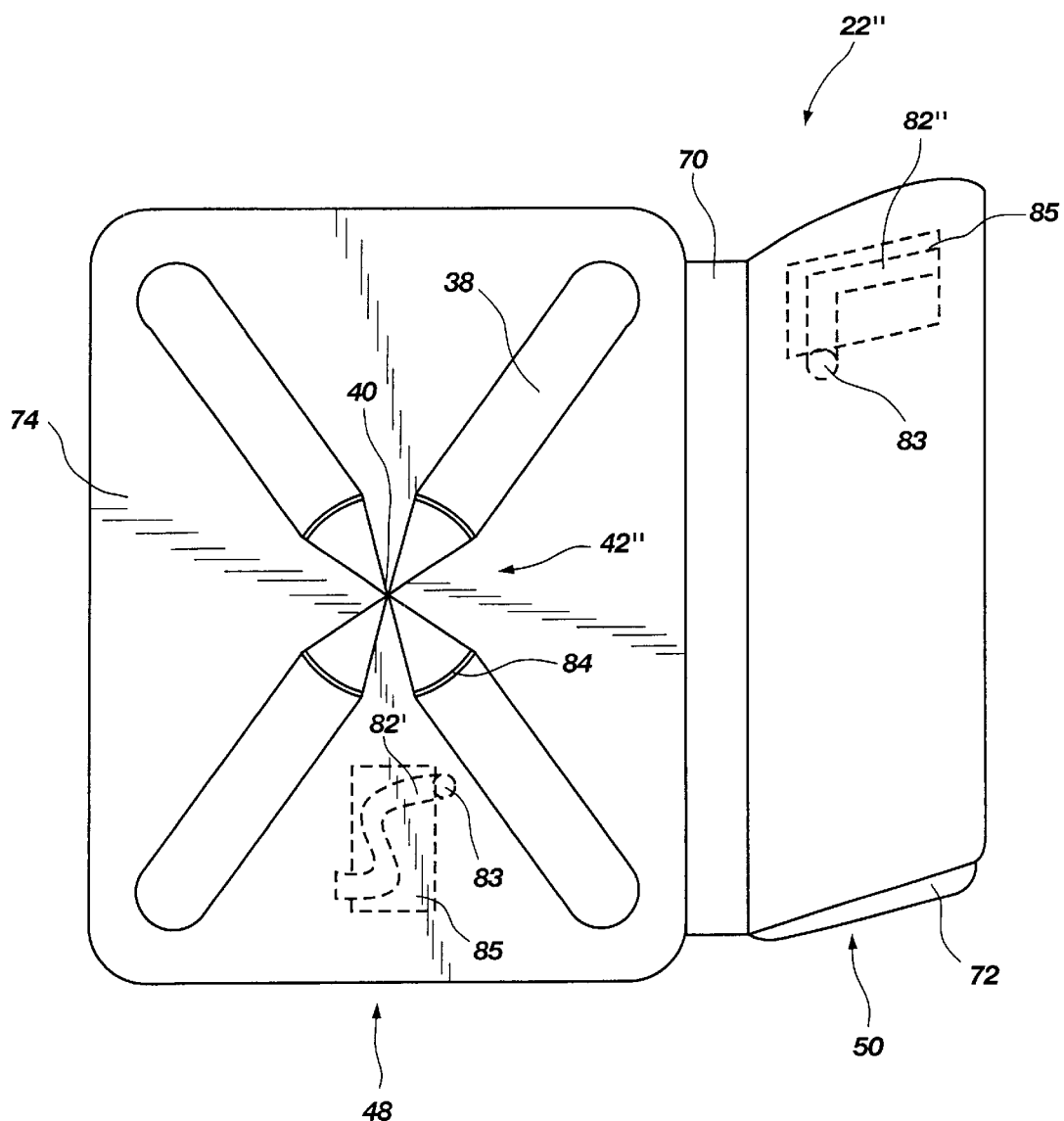
FIG. 5 illustrates a top view of one embodiment of an least one containment layer for a waste collection system of the present invention.

In FIG. 5, the first containment layer 22" is shown including first segment 48 attached to a second segment 50 via a hinge element 70. Thus, the first segment 48 of the first containment layer 22" may be secured firmly over a first chamber 26 (not shown) while the attached second segment 50 of the first containment layer 22" may be positioned to alternately expose or cover a second chamber 28 (not shown). For example, a user may securely fasten a first segment 48 over a chamber configured to receive fluid while alternately exposing and covering a chamber configured to receive particulate waste or to serve as a storage compartment. If desired, the first containment layer 22" may include a tab 72 to assist in the detachment of the first containment layer 22" from the receptacle 20 (not shown).

FIG. 5 also depicts an alternate embodiment of the valve member 42" wherein the valve member 42" is formed of molded plastic such that it is an integral part of the first containment layer 22". Thus, the valve member 42" may extend from either the sides of the channels 38 or the perimeter of the opening 40 such that a gap 84 is formed between the valve member 42" and the channels 38. Thus, fluid on the surfaces 74 or in the channels 38 of the first containment layer 22" may enter the opening 40 either through the valve member 42" or through the gap 84 between the valve member 42" and the channels 38.

FIG. 5 also illustrates alternate embodiments of the vent 82 formed within a first containment layer 22". The vent 82 may comprise an S-shaped recess 82' or an L-shaped recess 82" terminating in an aperture 83 (shown in dotted lines) in containment layer 22" having a piece of adhesive-coated tape 85 located over at least a portion thereof inserted into the receptacle 20 so that air or other gases may escape from the receptacle 20, but fluids are contained therein.

Figure 6:
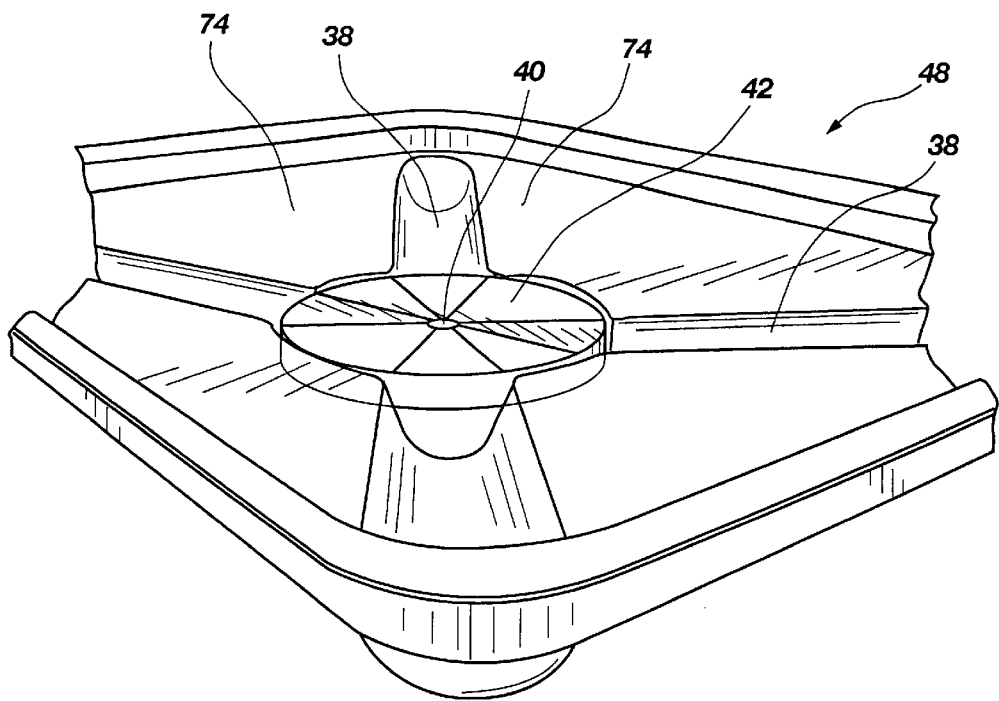
FIG. 6 is a perspective view of an at least one containment layer and valve member of one embodiment of a receptacle of a waste collection system of the present invention.
Figure 7:
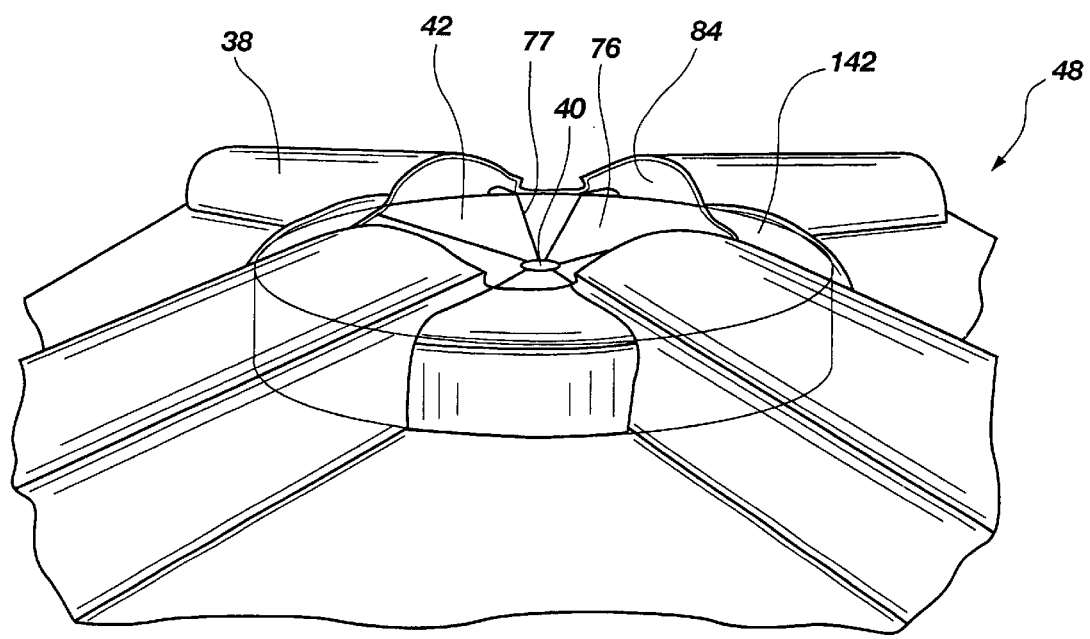
FIG. 7 is a perspective view from the underside of an at least one containment layer and valve member of one embodiment of a receptacle of a waste collection system of the present invention.

FIG. 6 and FIG. 7 illustrate an alternate view of one embodiment of the present invention wherein the first containment layer includes a foam valve member 42. FIGS. 6 and 7 illustrate a first segment 48 of the first containment layer 22 including downward sloping surfaces 74 and a plurality of channels 38 that converge upon an opening 40. Thus, fluids on the first containment layer 22 are directed toward the opening 40 which may drain into a receptacle 20 below (not shown). While FIGS. 6 and 7 depict the opening 40 as substantially circular, the opening 40 may be frustoconical, funnel-shaped or any other desired shape. Further, the opening 40 may be shaped such that a fluid delivery device, such as a syringe, beaker, or plastic tubing, is prevented from penetrating too far into the receptacle 20. For example, the opening 40 may include a stop below the surface of the opening that prevents the tip of a syringe from contacting contents within the receptacle 20 (not shown in FIGS. 6 or 7).

Referring to FIGS. 6 and 7, a channel 38 may be formed between each pair of sloping surfaces 74 such that each channel 38 runs beneath the valve member 42. The channels 38 may be wider and deeper than known embodiments to assist in collecting and draining fluid. Thus, channels 38 permit fluids that contact the surface of the first containment layer 22 to be quickly fed and drained into the interior of receptacle 20. The valve member 42 may rest on a ledge 142 around the opening 40 such that the valve member 42 does not block the channels 38. As shown in FIG. 7, in one embodiment, the channels 38 are configured such that a gap 84 is formed between the channel 38 and a valve member 42 to further expedite drainage of fluids in the channels 38. Thus, a small volume of fluid will quickly drain beneath the valve member 42 through the gap 84. When a larger volume of fluid is present, it will pass through both the gap 84 as well as the valve member 42. Thus, the risk of splashing is decreased and the rate of drainage into the receptacle 20 is increased.

Figure 8:
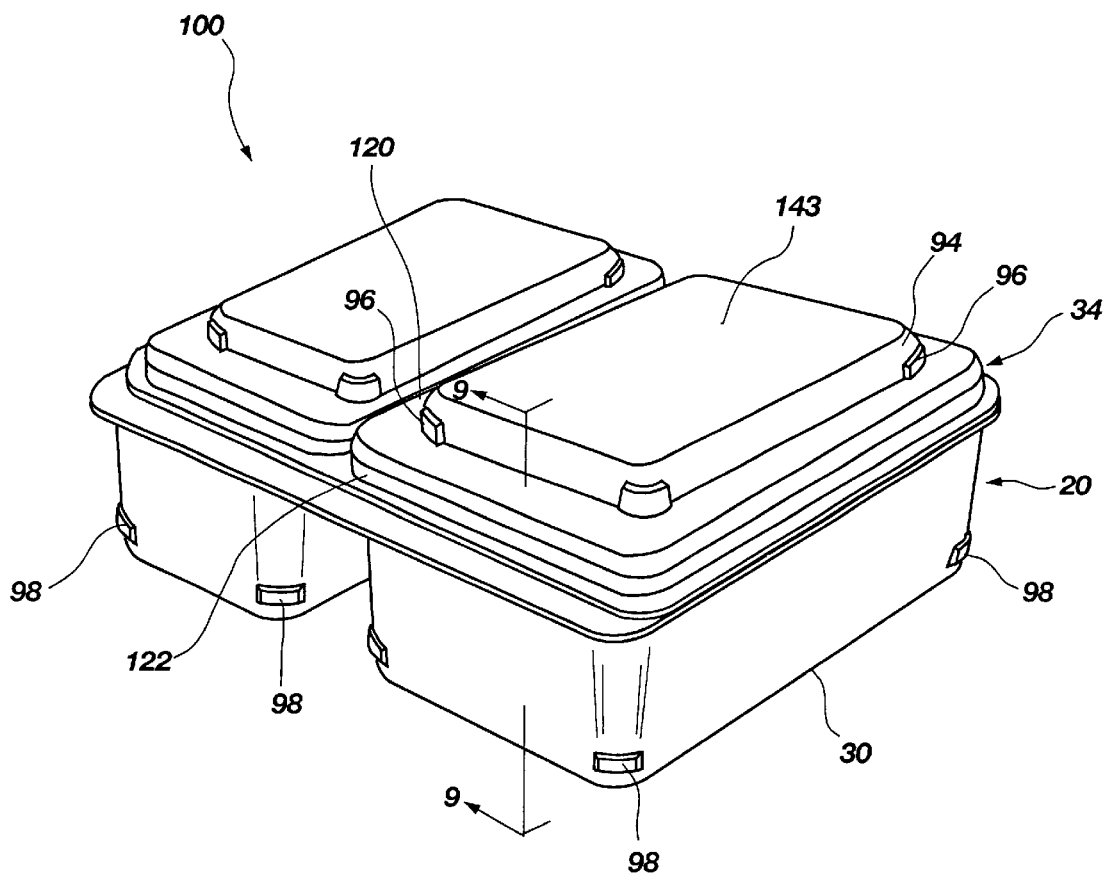
FIG. 8 illustrates a perspective view of one embodiment of a waste collection system of the present invention.

FIG. 8 illustrates an embodiment of the waste collection system 100 wherein a second containment layer 34 has been placed on top of receptacle 20 so as to enclose the receptacle 20 and all chambers thereof for permanent disposal. The second containment layer 34 may include a plurality of pockets 96 within a recess 94 that are configured to accept detents 98 on the side of the receptacle 20. Thus, when the second containment layer 34 is used to stabilize the receptacle 20, the bottom 30 of the chambers of receptacle 20 may be placed within the recess 94 of the second containment layer 34 such that the detents 98 fit securely within the pockets 96 (not shown in FIG. 8). In an alternate embodiment, the second containment layer 34 may include a non-skid or skid-resistant surface formed on an uppermost surface 143 thereof. The top of the second containment layer 34 is shown including a horizontal rim 120 that extends from recess 94 to a third shoulder 122.

Figure 9:
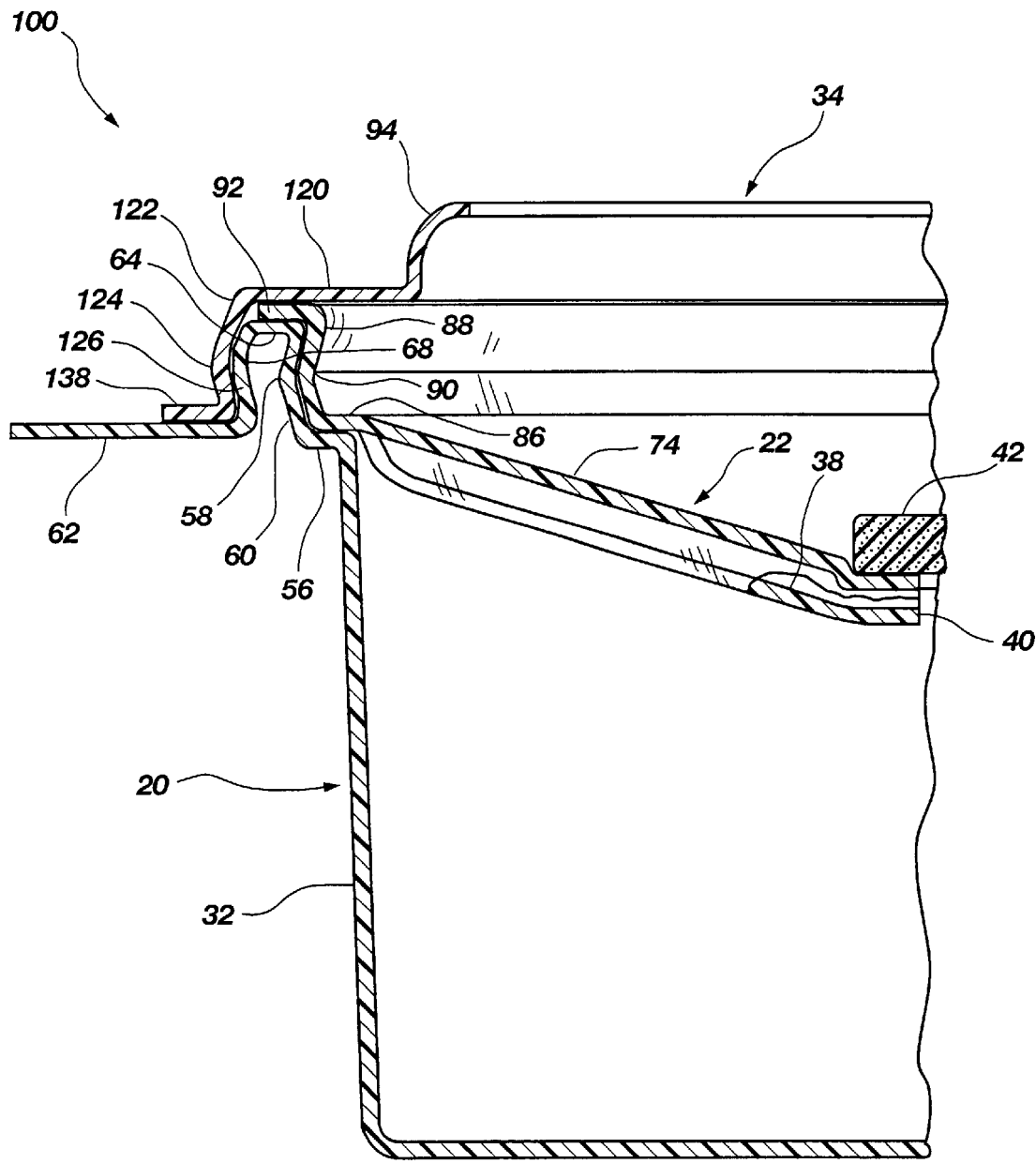
FIG. 9 is a cross-sectional view taken along line 9—9 of FIG. 8.

FIG. 9 illustrates one embodiment of the first containment layer 22 and second containment layer 34 retained against the receptacle 20. As shown in FIG. 9, the sidewalls 32 of the chambers of receptacle 20 may include a horizontal first shoulder 56 formed near the top thereof and joined to an inner wall 60 that may be bent at a point 58 so that the inner wall 60 is slightly concave. The inner wall 60 continues and may be joined by a small horizontal member 64 to an outer sidewall 126. The outer sidewall 126 may also be similarly bent at point 68 so that it is slightly convex. The outer sidewall 126 may terminate at its lower end in a horizontal rim or shelf 62 that extends around the entire periphery of receptacle 20 or around each chamber therein. The inner wall 60 and outer sidewall 126 together form the snap ring 66 (shown in FIG. 2), which may be used to provide engagement with other parts of the waste collection system 100, both during collection of contaminated fluids, and for later closure of the contaminated fluids, once the entire waste collection system 100 is ready for permanent disposal. The first containment layer 22 may be used such that fluid is presented onto the sloping surfaces 74 of the first containment layer 22 for drainage through the channels 38, or conveyed directly into the opening 40.

The first containment layer 22 may attach to the receptacle in a variety of ways. One embodiment shown in FIG. 9 illustrates the first containment layer 22 including a rim 86 which extends around the periphery of the first containment layer 22 and which sits upon first shoulder 56 of sidewalls 32 of receptacle 20. The rim 86 may be formed as a unitary part of a second shoulder 88 which extends horizontally and which is bent at 90 to correspond with the bend 58 in the inner wall 60 of snap ring 66 on receptacle 20. The second shoulder 88 terminates in an upper horizontal member 92 which sits in a corresponding fashion over the horizontal member 64 of snap ring 66. The dimensions of first containment layer 22 relative to the open top of receptacle 20 are such that, as shown in FIG. 9, the second shoulder 88 fits in a friction fit over the horizontal member 64 and inner wall 60 of snap ring 66 so as to provide a primary retaining layer between the receptacle 20 and first containment layer 22. Alternatively, the first containment layer 22 and receptacle 20 engage by way of a grooved or screw top or sealing film (not shown in FIG. 9). In yet another embodiment, the first containment layer 22 may be continuous with the sidewalls 32 of the chambers of receptacle 20 (not shown in FIG. 9).

The second containment layer 34 may also include a horizontal rim 120 that extends from recess 94 to a third shoulder 122 bent at point 124 corresponding to the bend 68 in the outer sidewall 126 of snap ring 66 on receptacle 20. The third shoulder 122 may terminate in a small horizontal extension 138 that extends around the periphery of the second containment layer 34. Accordingly, second containment layer 34 may be configured so the third shoulder 122 fits over the horizontal member 92 of first containment layer 22 and over the outer sidewall 126 of snap ring 66 in a close fit provided by the bent configuration of the outer sidewall 126 and the corresponding bent configuration of the third shoulder 122. Thus, the third shoulder 122 of the second containment layer 34 provides a closure between both the first containment layer 22 and the receptacle 20. Thus, the use of both the first containment layer 22 and second containment layer 34 provides a double barrier for the receptacle 20. This helps contain waste in the receptacle 20 during transport of the waste collection system 100 to an incinerator or other permanent disposal site.

Further, it will be understood that the waste collection system 100 may be used with only the second containment layer 34 and not the first containment layer 22. Similarly, in an alternate embodiment, the waste collection system 100 only includes the first containment layer 22 and not a second containment layer 34. In such an embodiment, a shield may be used to cover an opening 40 within the first containment layer 22 during transport (not shown).

Figure 10:
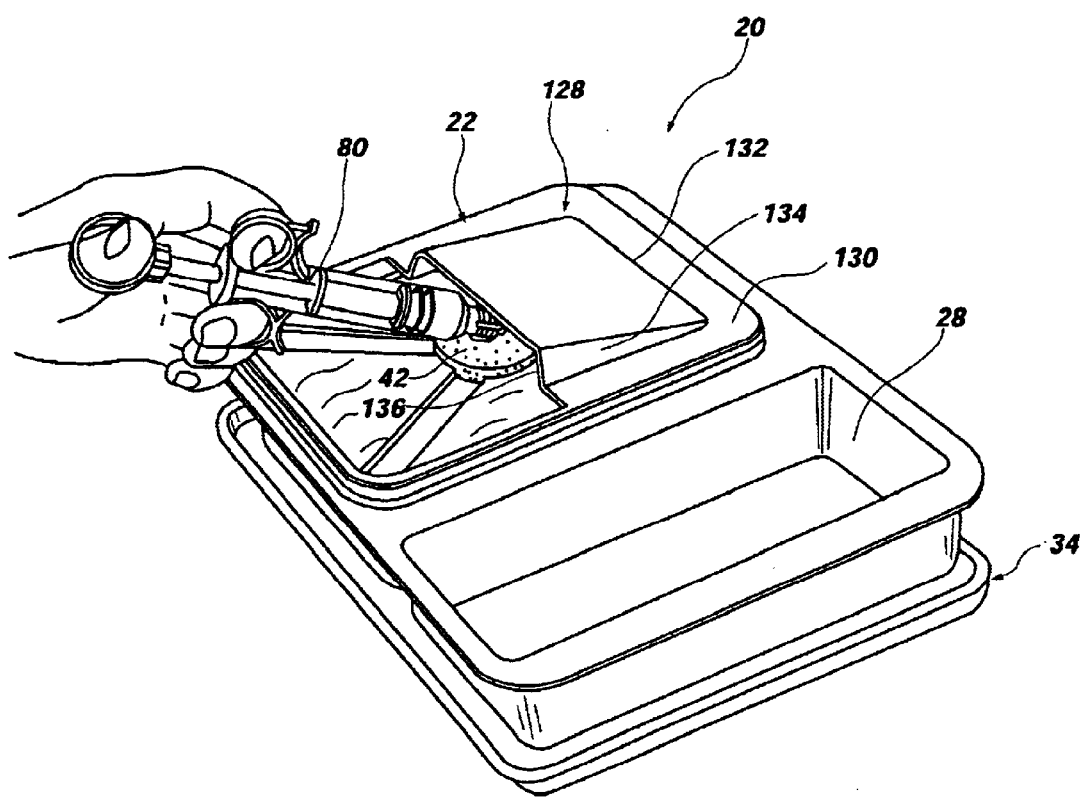
FIG. 10 is a perspective view of an at least one containment layer and hood attached to one embodiment of a receptacle of a waste collection system of the present invention.

In another embodiment of the present invention shown in FIG. 10, a substantially square receptacle 20 may include a first containment layer 22 having a hood 128 covering at least a portion of the first containment layer 22. The hood 128 decreases the risk of fluids dropped or expelled onto the first containment layer 22 splashing above the first containment layer 22. FIG. 10 also illustrates a second containment layer 34 attached to the bottom of the chamber of the receptacle 20 to stabilize the receptacle 20 during waste collection. As shown, a second chamber 28 may be used to collect particulate waste.

The hood 128 may be assembled to the first containment layer 22. Thus, as shown in FIG. 10, first containment layer 22 may include a horizontal surface 130 that meets the hood 128 at the downwardly tapering edge 132, with hood 128 being provided with tapered sides 134 which terminate in an aperture 136. The hood 128 may extend over approximately half of the first containment layer 22. As illustrated in FIG. 101 a syringe 80 may be inserted into the aperture 136 for purposes of injecting contaminated fluids onto the valve member 42 or directly into the opening 40 (not shown). However, the hood 128 provides added protection against any fluids that are splashed, thereby further helping to contain fluids so that they do not contact personnel.

In one embodiment, the hood 128 is designed so that the height of aperture 136 is such that the entire hood 128 will fit within the recess 94 (FIG. 9) of second containment layer 34 when placed onto the top of receptacle 20 after the waste has been collected and the receptacle 20 is engaged by the second containment layer 34 for containment of the waste prior to permanent disposal of the entire waste collection system 100 (not shown).

Figure 11:
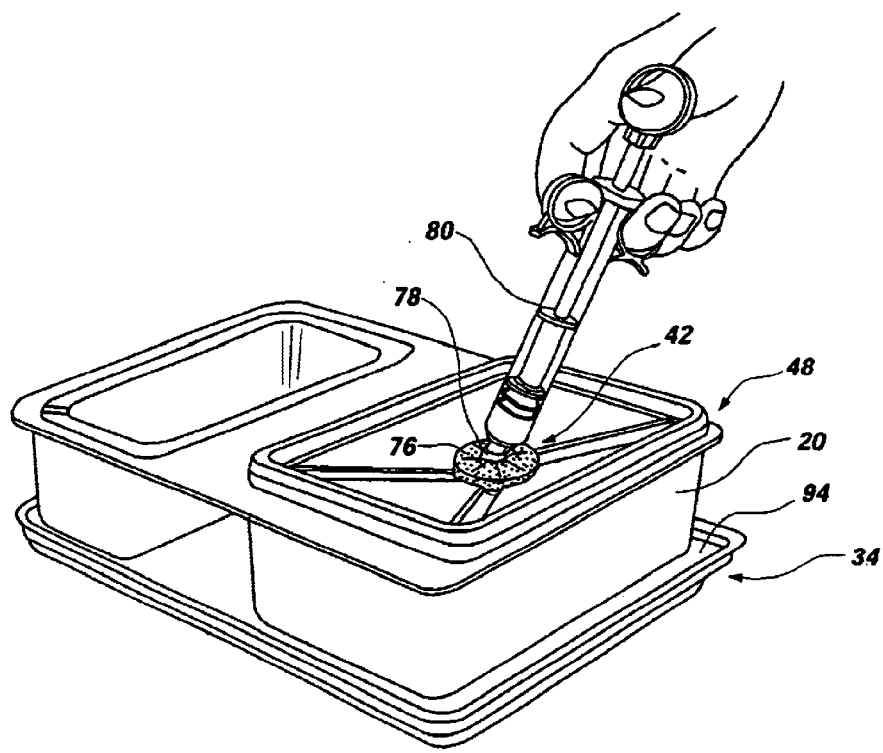
FIG. 11 is a perspective view of one embodiment of a receptacle of a waste collection system of the present invention.

FIG. 11 depicts one embodiment of the present invention wherein a fluid delivery device, such as a syringe 80, is inserted into the valve member 42. The flaps 76 of the valve member 42 accept the tip 78 of the syringe 80 and allow access to the interior of receptacle 20. Flaps 76 help reduce the risk of splashing above a first segment 48 of the first containment layer while fluid is delivered into the receptacle 20. In FIG. 11, the second containment layer 34 is shown receiving the receptacle 20 in a friction-tight fit so as to provide stabilizing support to receptacle 20 when the receptacle 20 is placed on a surface. In this configuration, during waste collection, the second containment layer 34 helps to prevent the receptacle 20 from excessive movement.

Figure 12:
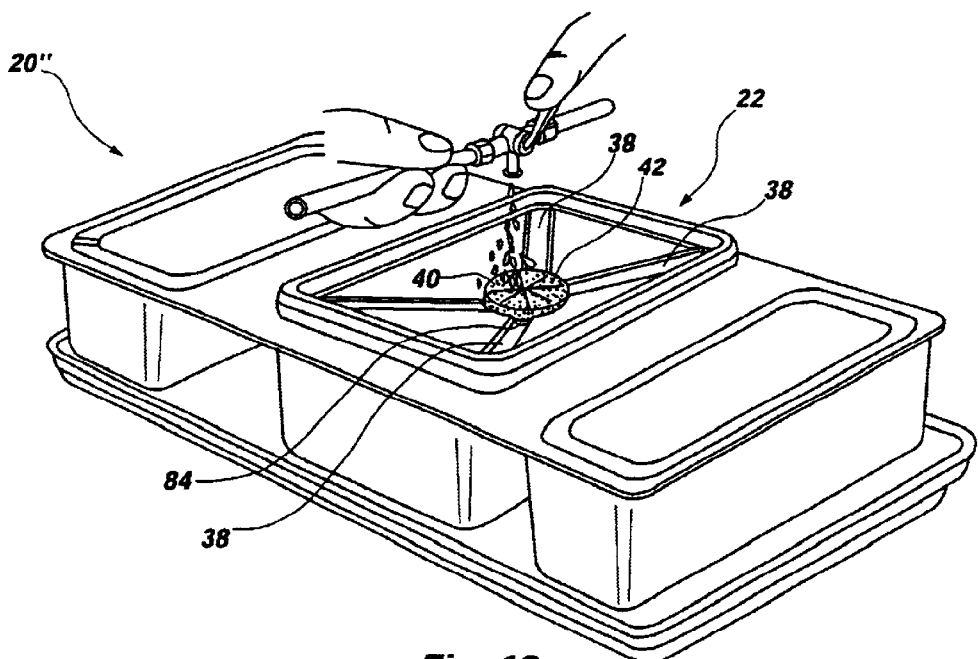
FIG. 12 is a perspective view of one embodiment of a receptacle of a waste collection system of the present invention.

FIG. 12 illustrates an embodiment of the present invention wherein the receptacle 20" includes three chambers. At least one chamber is configured to accept fluids and includes a first containment layer 22 having a plurality of channels 38 therein draining toward an opening 40. A valve member 42 may optionally be positioned adjacent the opening 40. Fluids may be delivered to the first containment layer 22 in a variety of ways. Fluids may be dropped directly onto the surface of the first containment layer 22 and drain by the channels 38 to the interior of receptacle 20, either through the gap 84 or through the valve member 42. Alternatively, the fluid delivery device depicted in FIG. 11 may be inserted into the valve member 42 and drained directly into the receptacle 20. While FIG. 12 illustrates fluids being drained from tubing, it will be understood that fluids may be delivered to the receptacle 20 in a variety of manners including, for example, through a beaker, glass or syringe.

Figure 13:
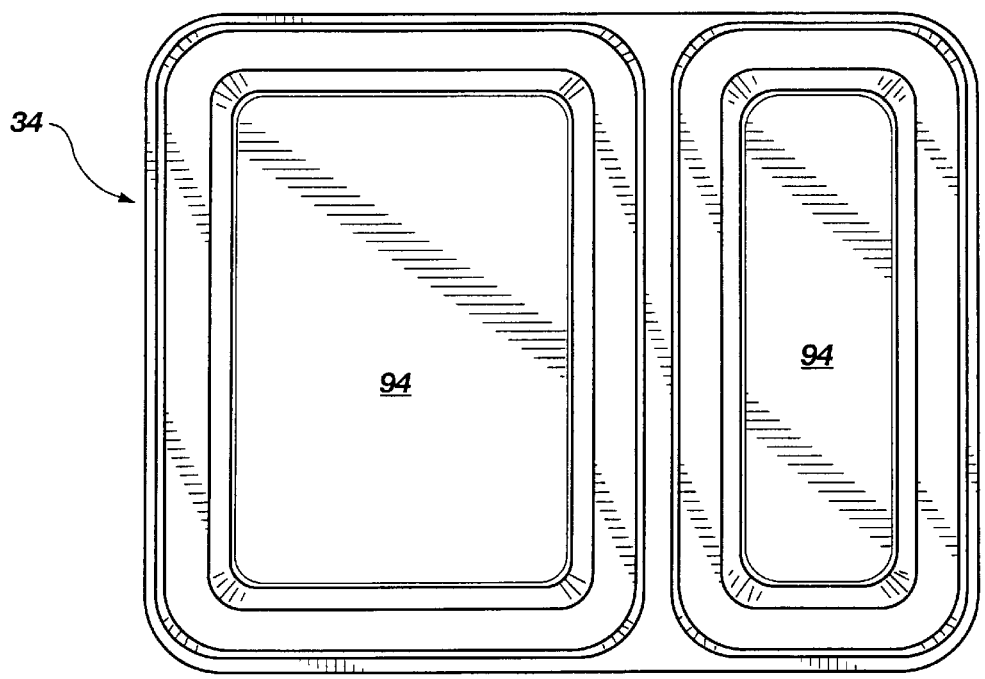
FIG. 13 is a top view of an at least one containment layer positioned for use as a stabilizing base for one embodiment of a receptacle of a waste collection system of the present invention.
Figure 14:
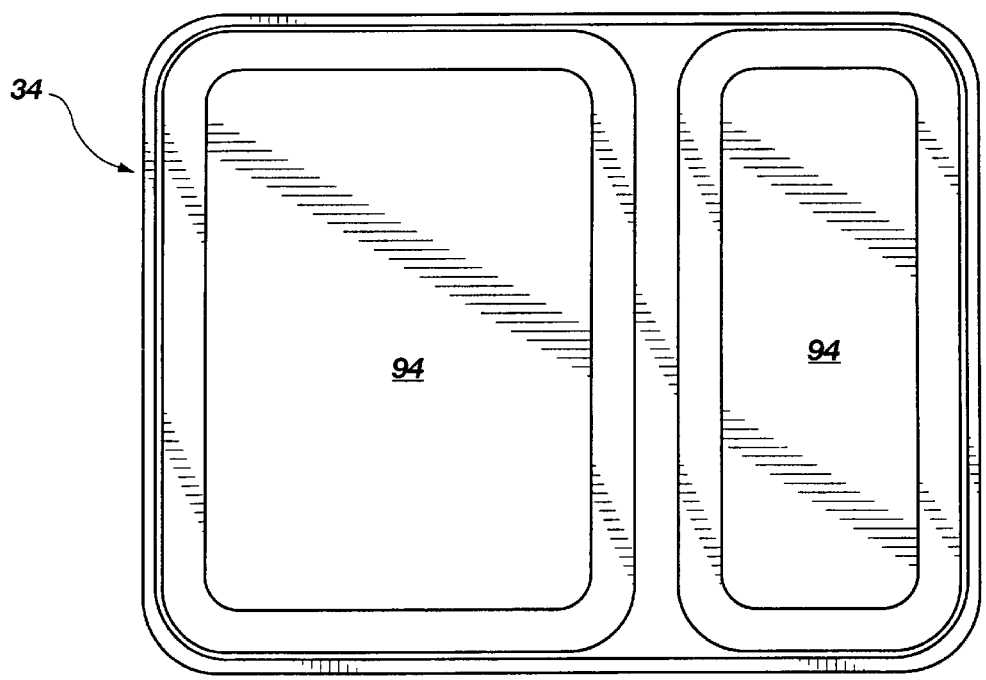
FIG. 14 is a top view of an at least one containment layer of one embodiment of a receptacle of a waste collection system of the present invention.

FIG. 13 depicts one position of the second containment layer 34 prior to accepting the bottom 30 of a chamber of receptacle 20. The second containment layer 34 may be positioned on a surface such that at least one recess 94 configured to accept the bottom 30 of a chamber of the receptacle 20 is exposed. The second containment layer 34 illustrated in FIG. 13 is configured to accept a two-chambered receptacle 20 (not shown). FIG. 14 illustrates a top view of one embodiment of the second containment layer 34 attached to a receptacle 20 (not visible).

Figure 15:
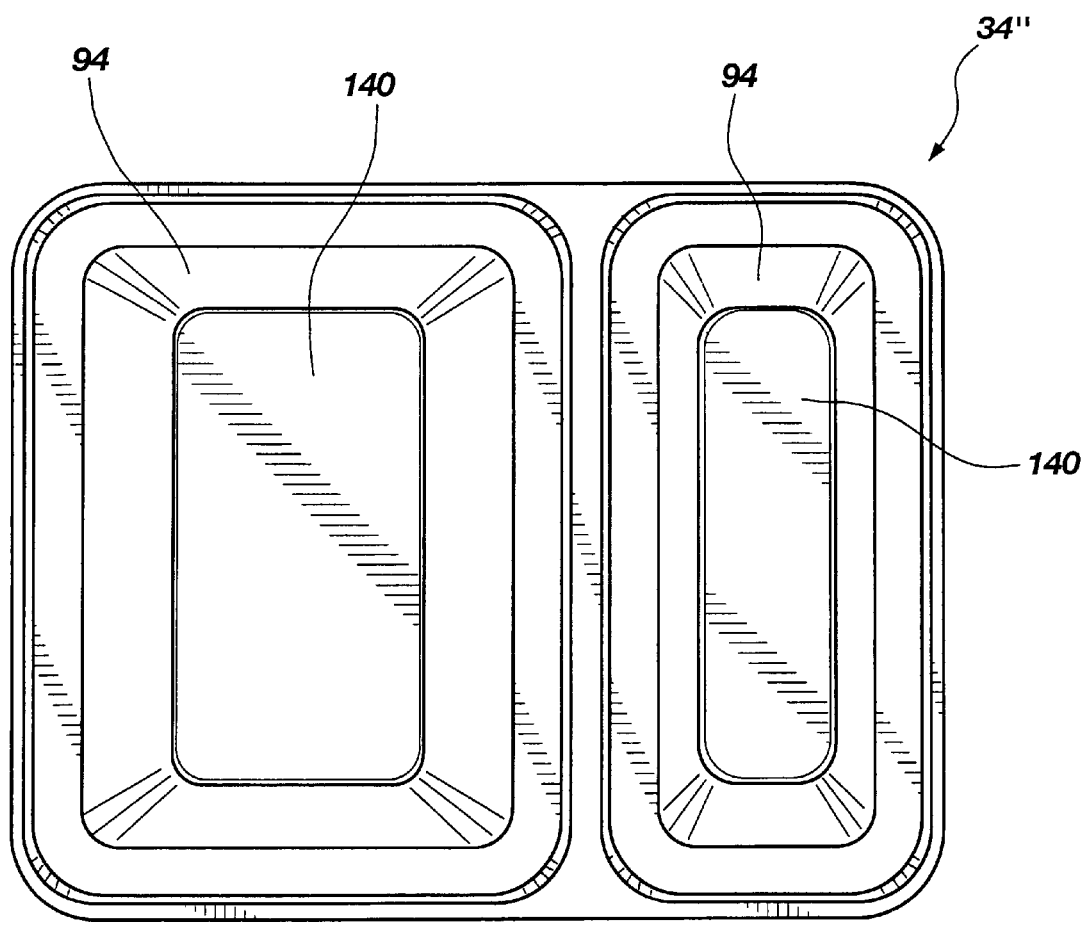
FIG. 15 is a top view of an at least one containment layer of one embodiment of a receptacle of a waste collection system of the present invention.

In an alternate embodiment shown in FIG. 15, the second containment layer 34" includes a recess 94 for accepting and stabilizing the bottoms of chambers of the receptacle 20 (not shown). The second containment layer 34" further includes a nook 140 (two shown in FIG. 15) that may comprise a raised or slightly sunken area within the recess 94. When the second containment layer 34" is functioning as a stabilizing means, the nook 140 may function to raise the second containment layer 34" above a work surface to decrease the possibility that the second containment layer 34" is resting in contaminated fluid. When the second containment layer 34" is functioning as a cover for the receptacle 20, the nook 140 may function to accept and stabilize the bottom of a second receptacle of a second waste collection system that has been stacked on top of the second containment layer 34". Thus, personnel may be able to transport several stacked full waste collection systems 100 more easily.

Figure 16:
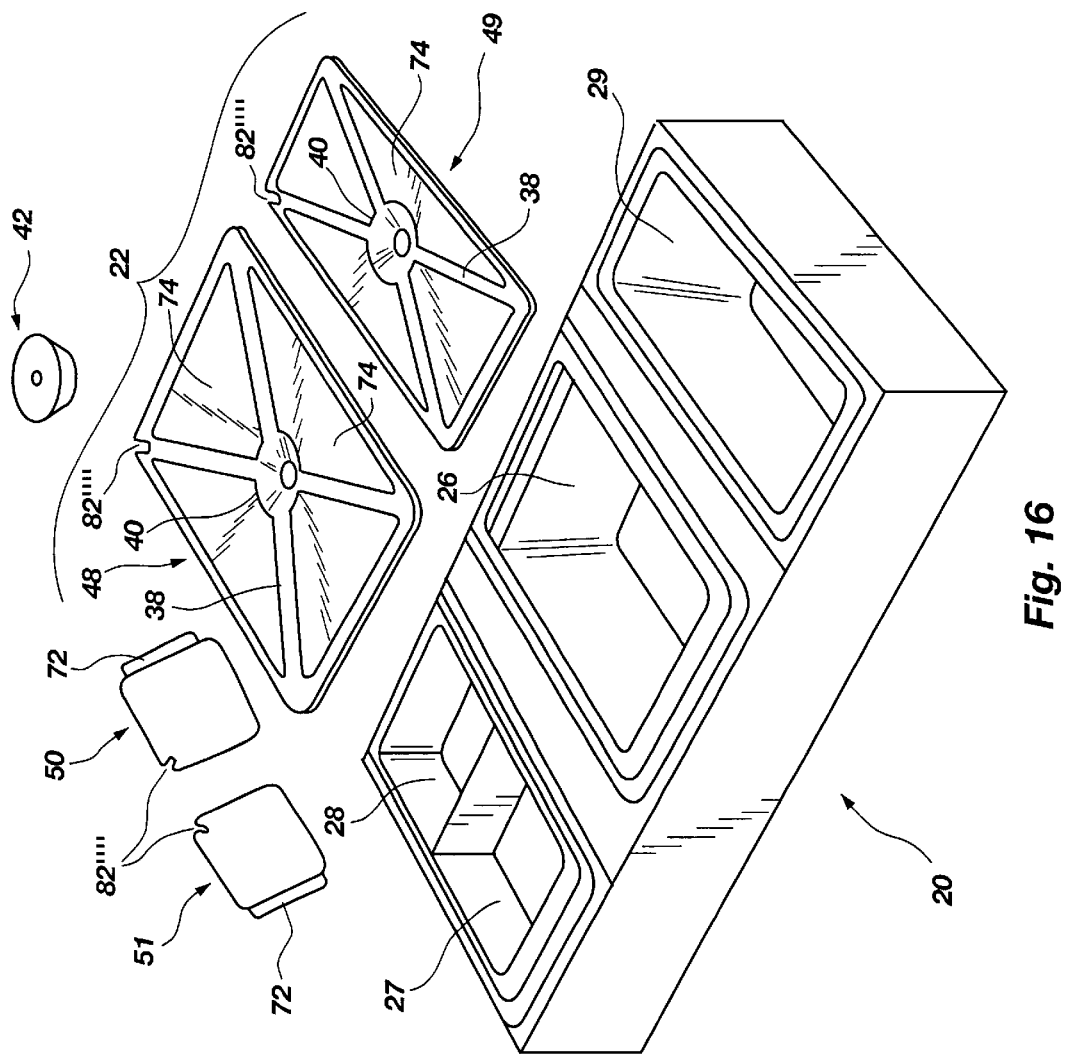
FIG. 16 is an exploded perspective view of one embodiment of a multi-chambered receptacle and at least one containment layer of a waste collection system of the present invention.

FIG. 16 depicts another embodiment of the present invention including a multi-chambered receptacle 20 including a first chamber 26 for receiving fluid, second chamber 28, third chamber 29 and fourth chamber 27 for receiving fluid. Thus, it will be understood that the receptacle 20 may include any number of chambers having different shapes. In one embodiment, the first containment layer 22 includes a plurality of segments (48, 49, 50, 51) shaped to cover the plurality of chambers within the receptacle 20. Thus, it will be understood that the first containment layer 22 may include a separate segment for each chamber of the receptacle. As shown in FIG. 16, a first segment 48 may cover a first chamber 26. The first segment 48 may include a plurality of surfaces 74 sloping toward an opening 40 that may be funnel-shaped. In FIG. 16, the opening 40 is depicted as being slightly off-center. Channels 38 may be formed between each surface 74 and may drain into the funnel-shaped opening 40. The first segment 48 may also include a vent 82"" that allows air or any atmosphere to escape from a covered first chamber 26. FIG. 16 also illustrates a funnel-shaped valve member 42 that may be used with the first segment 48.

A second segment 50 and fourth segment 51 may be shaped to cover a second chamber 28 and fourth chamber 27 respectively and may each include a vent 82"" and a tab 72 that assists in the removal of the second segment 50 and fourth segment 51 from the chambers 28, 27. As shown in FIG. 16, a third segment 49 may cover a third chamber 29. The third segment 49 may include a plurality of surfaces 74 sloping toward an opening 40 that may be frusto-conical in shape. Channels 38 may be formed between each surface 74 and may drain into the frusto-conical-shaped opening 40. The third segment 49 may also include a vent 82"" that allows air or any atmosphere to escape from a covered third chamber 29.

Figure 17A:
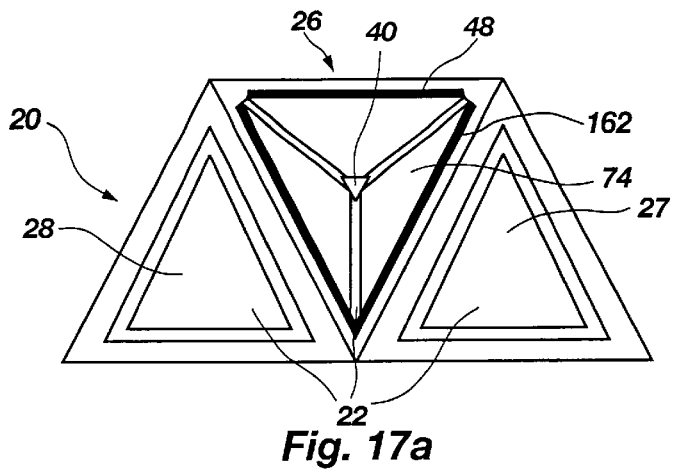
FIG. 17a is a top view of one embodiment of a trapezoidal receptacle and at least one containment layer of a waste collection system of the present invention.
Figure 17B:
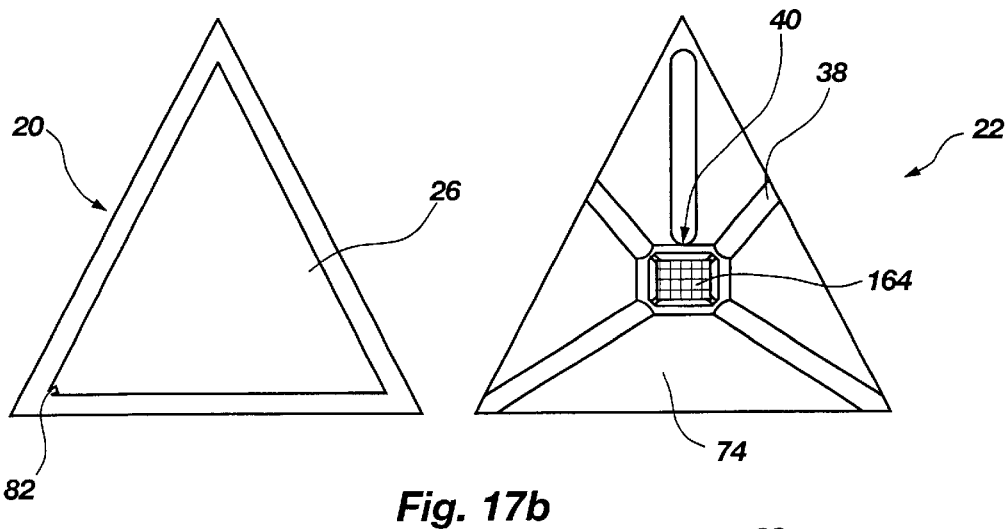
FIG. 17b is a top view of one embodiment of a triangular receptacle and at least one containment layer of a waste collection system of the present invention.
Figure 17C:
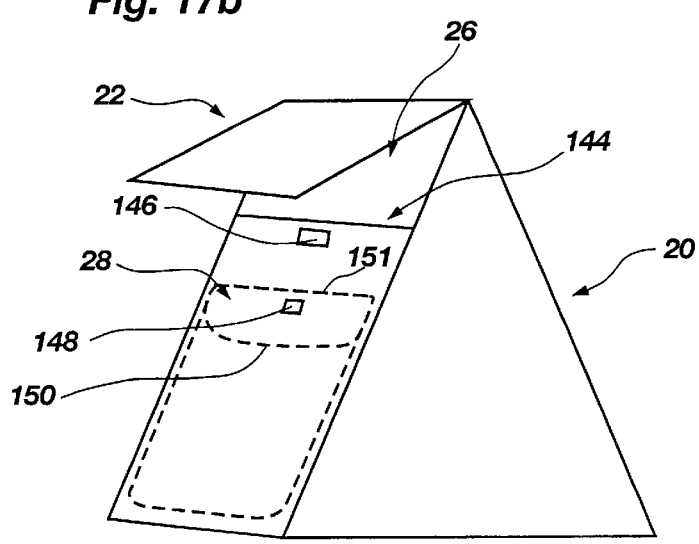
FIG. 17c is a side perspective view of a pyramidal receptacle of a waste collection system of the present invention.

FIGS. 17*a*, 17*b* and 17*c* illustrate substantially triangular receptacles 20. In FIG. 17*a*, the receptacle 20 is substantially trapezoidal and includes three joined substantially triangular chambers (26, 27, 28) configured to receive and retain waste. FIG. 17*a* depicts each chamber as including a segment of a first containment layer 22. A first segment 48 of the first containment layer 22 may be positioned over a first chamber 26. Sealing tape 162 may be placed around the perimeter of the first segment 48 to cover the junction between the first segment 48 and the first chamber 26. The first segment 48 may include a plurality of surfaces 74 sloping toward an opening 40 that may be substantially triangular in shape. Channels 38 may be formed between each surface 74 and may drain into the triangularly shaped opening 40.

FIG. 17*b* illustrates another embodiment of a triangular receptacle 20 of the present invention having a first chamber 26 including a vent 82. While FIG. 17*b* depicts the receptacle 20 as having a single chamber, it will be understood that the receptacle 20 may include any number of chambers as described herein. FIG. 17*b* also includes a first containment layer 22 shaped to cover the first chamber 26 and may include a plurality of surfaces 74 sloping toward an opening 40 that may be substantially square in shape. Channels 38 may be formed between each surface 74 and may drain into the square-shaped opening 40. The opening 40 may include a stop 164 below the surface of the opening 40 that may prevent a fluid delivery vehicle from penetrating too deeply into the receptacle 20.

FIG. 17*c* illustrates one embodiment of the present invention including a pyramidal-shaped receptacle 20 having a first chamber 26 and a second chamber 28. The first chamber 26 may include an exposed surface 144 for receiving fluid waste and may include a first containment layer 22 attached thereto that covers the exposed surface 144. An adhesive tab 146 may attach the moveable portion of the first containment layer 22 to the receptacle 20. The second chamber 28 is depicted as a pouch on the side of the receptacle 20 that may accept particulate waste or store various objects. A second adhesive tab 148 may close a first side 150 of the second chamber 28 against a second side 151.

Figure 18A:
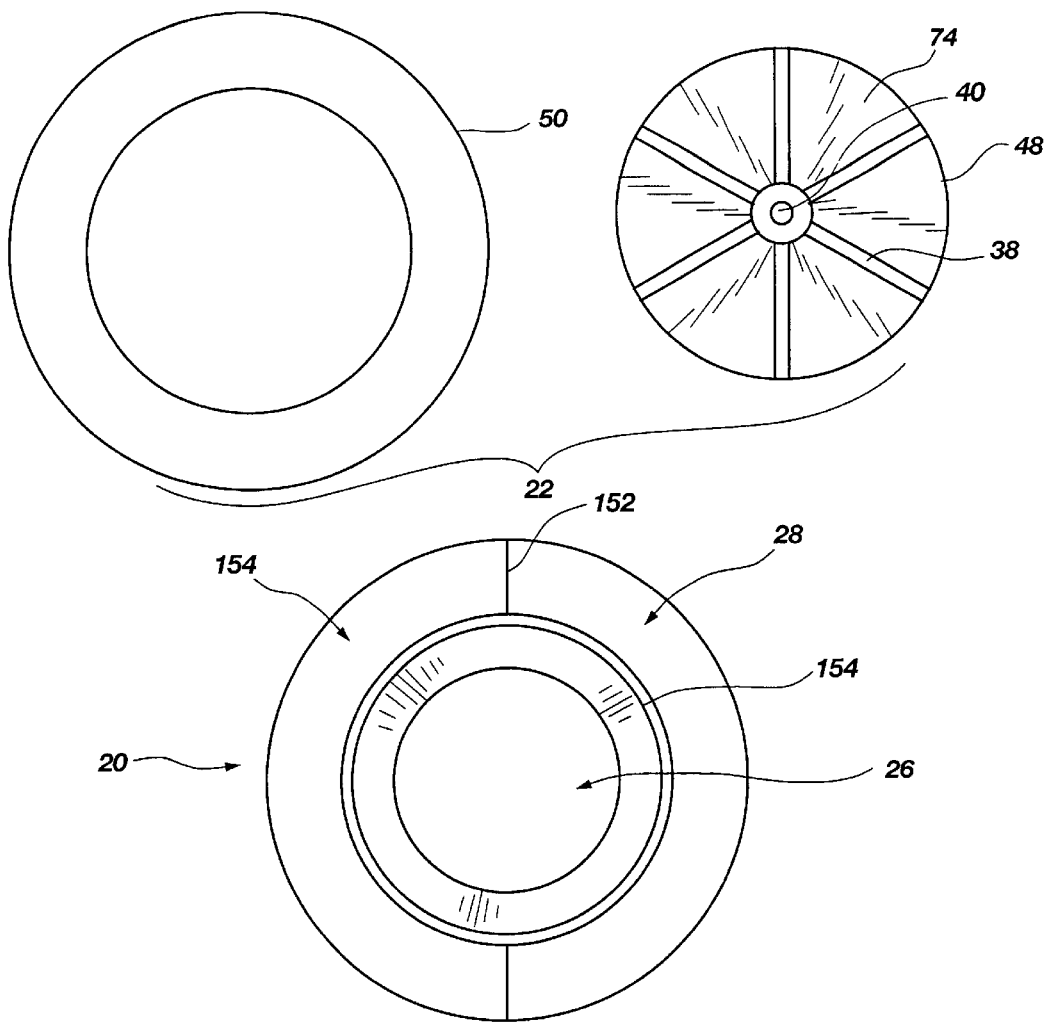
FIG. 18a is a top view of a circular receptacle and at least one containment layer of a waste collection system of the present invention.

FIG. 18a illustrates another embodiment of the present invention including a circularly shaped receptacle 20 including two concentric circular chambers. A first chamber 26 may receive fluids. A second chamber 28 may receive particulate waste or store objects used in waste collection. The second chamber 28 may include at least one partition 152 that divides the second chamber 28 into several smaller chambers. A first containment layer 22 may include a first segment 48 that may cover the first chamber 26 by screwing into grooves 154 around the perimeter of the first chamber 26. The first segment 48 may include a plurality of sloping surfaces 74 that drain toward a central opening 40. A plurality of channels 38 may be formed between the plurality of sloping surfaces 74. A second segment 50 of the first containment layer 22 may cover the second chamber 28 by screwing into grooves 154 around the perimeter of the first chamber 26.

Figure 18B:
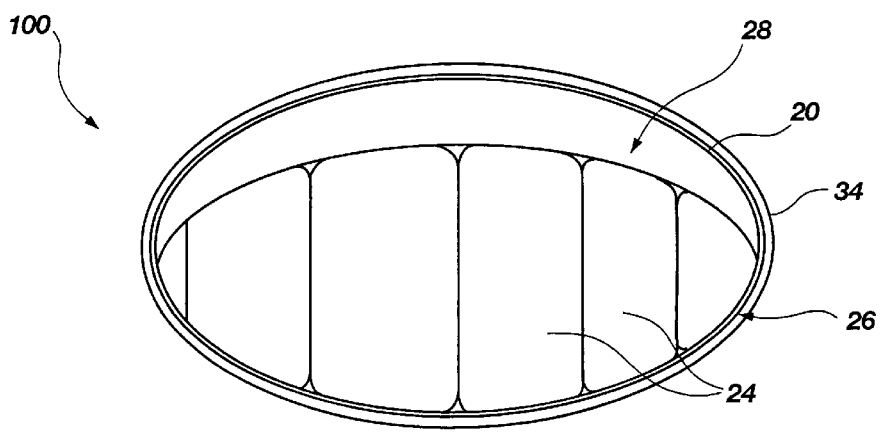
FIG. 18b is a top view of an oval-shaped receptacle of a waste collection system of the present invention.

Referring to FIG. 18b, an oval-shaped receptacle 20 is shown having a first chamber 26 and a second chamber 28. In one embodiment, fluids or other waste may be delivered directly to a receptacle 20 without the use of a first containment layer 22. If desired, the receptacle 20 may include at least one absorbent layer 24 and the second containment layer 34 may be used to stabilize the open-topped receptacle 20 during waste collection. In this embodiment, the waste is deposited directly into a chamber within receptacle 20 and onto the absorbent layer 24. However, the absorbent layer 24 may not be desired if a chamber is not accepting fluid waste. After the waste has been collected in receptacle 20, the second containment layer 34 may be removed from the bottom 30 of a chamber of the receptacle 20 and placed onto the snap ring 66 in a friction-tight fit to substantially retain the waste collected in receptacle 20 and held by absorbent layer 24 (not shown in FIG. 18b). Optionally, the waste collection system 100 may be utilized without using either an absorbent layer 24 or a first containment layer 22 such that waste is placed directly into the receptacle 20 and then the receptacle 20 is substantially retained (not shown).

Figure 19A:
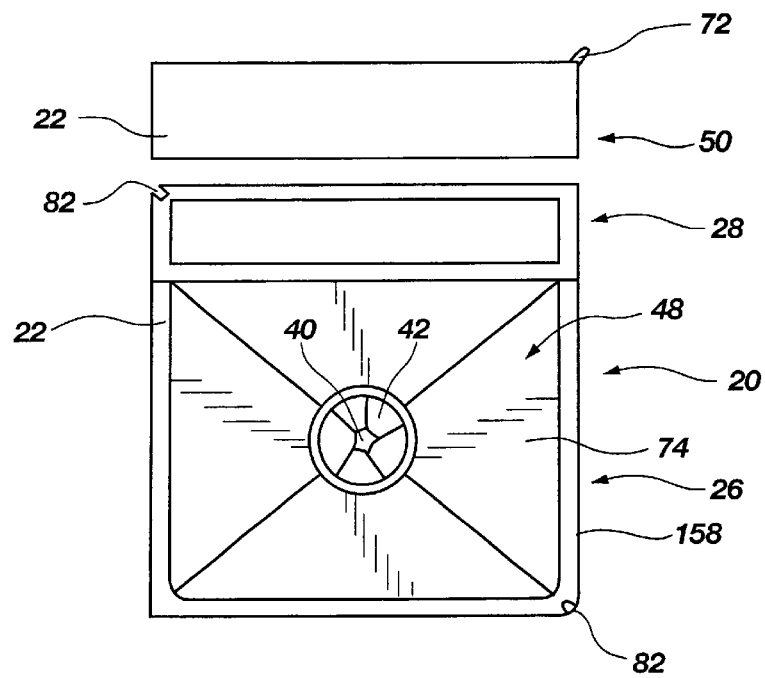
FIG. 19a is a top view of a unitary receptacle and at least one containment layer of a waste collection system of the present invention.
Figure 19B:
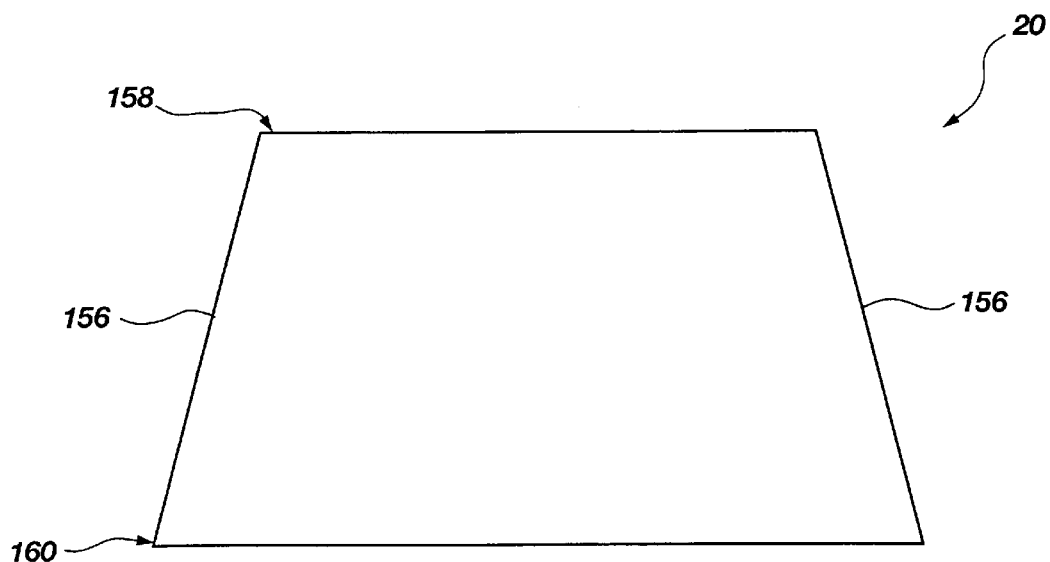

FIGS. 19a and 19b illustrate an embodiment of the present invention including a receptacle 20 having sides 156 that extend outwardly from a substantially square top 158 to a larger square base 160. A first segment 48 of a first containment layer 22 may be formed as a part of a first chamber 26 of the receptacle 20, for example, by casting techniques, as shown in FIG. 19a. The connected first segment 48 may include a plurality of surfaces 74 sloping toward an opening 40. A rubber valve member 42 may be positioned proximate the opening 40. A second segment 50 of the first containment layer 22 may cover a second chamber 28 of the receptacle 20 and may include a tab 72 to assist in removing the second segment 50 from the second chamber 28. The first chamber 26 and second chamber 28 may both include a vent 82 that allows air or any other atmosphere to escape from the covered chambers.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A waste collection system comprising:

a receptacle housing a first chamber and a second chamber flanking the first chamber, the second chamber configured to accept waste and including a bottom surface and at least one sidewall connected to the bottom surface, a first sidewall of the at least one sidewall including a lowermost portion proximate the bottom surface and an uppermost portion, the uppermost portion of the first sidewall including at least one vent; and at least one containment layer configured to substantially retain the waste within at least the second chamber.

2. The waste collection system of claim 1, wherein the at least one containment layer is configured to substantially retain the waste within the receptacle.

3. The waste collection system of claim 1, wherein the at least one containment layer comprises a plurality of surfaces sloping toward at least one opening therein.

4. The waste collection system of claim 3, further comprising a plurality of channels formed between the plurality of sloping surfaces, the plurality of channels configured to deliver the waste into the at least one opening.

5. The waste collection system of claim 3, wherein the at least one opening includes being one of a circular opening, funnel-shaped opening or frusto-conical opening.

6. The waste collection system of claim 3, further comprising a valve member positioned adjacent the at least one opening, the valve member configured to accept and retain waste below the at least one containment layer.

7. The waste collection system of claim 6, wherein the valve member comprises a funnel-shaped member or a circular disc.

8. The waste collection system of claim 6, wherein the valve member comprises at least one of foam, rubber and plastic.

9. The waste collection system of claim 8, wherein the valve member comprises a plurality of flaps extending from the at least one containment layer, the plurality of flaps surrounding a central aperture.

10. The waste collection system of claim 3, wherein the at least one containment layer comprises:

a plurality of channels formed between the plurality of sloping surfaces;

a ledge surrounding the at least one opening and between each channel of the plurality of channels; and a valve member positioned on the ledge such that a gap is formed between the valve member and the plurality of channels, wherein waste in the plurality of channels may enter the at least one opening through the gap.

11. The waste collection system of claim 1, wherein the at least one containment layer comprises a nook configured to accept a receptacle of a second waste collection system.

12. The waste collection system of claim 1, wherein the at least one containment layer is further configured to stabilize the receptacle.

13. The waste collection system of claim 1, further comprising at least one absorbent layer within the second chamber.

14. The waste collection system of claim 13, wherein the at least one absorbent layer comprises at least one of wood pulp filler, super-absorbent polymer filler, and water-based guar gel.

15. The waste collection system of claim 1, wherein the at least one containment layer further comprises an S-shaped or L-shaped recess.

16. The waste collection system of claim 1, wherein the second chamber is configured to accept fluid waste and the first chamber is configured to accept particulate waste or serve as a storage compartment.

17. The waste collection system of claim 1, wherein the at least one containment layer engages the receptacle by at least one of a snap ring, grooves and sealing film.

18. The waste collection system of claim 1, wherein the at least one containment layer comprises:
   a first containment layer including a plurality of surfaces sloping toward at least one opening; and
   a second containment layer configured to alternately stabilize the receptacle and cover the receptacle.

19. The waste collection system of claim 18, wherein the receptacle includes a plurality of sidewalls, wherein at least one sidewall of the plurality of sidewalls includes at least one detent and wherein the second containment layer includes at least one pocket for accepting the at least one detent.

20. The waste collection system of claim 1, wherein the at least one containment layer comprises:
   at least one opening providing access to the second chamber; and
   a hood partially covering the at least one opening.

21. The waste collection system of claim 1, wherein the at least one containment layer and the receptacle are formed as a unitary plastic member.

22. A waste collection system comprising:
   a basin including at least one chamber configured to receive and retain fluids, the at least one chamber including a bottom surface and at least one sidewall extending substantially upward from the bottom surface to an upper rim;
   a first containment layer at least partially engaging the upper rim of the at least one chamber, the first containment layer including at least one aperture for receiving waste; and
   a vent associated with the upper rim of the at least one chamber.

23. The waste collection system of claim 22, wherein the at least one chamber includes a first chamber and a second chamber flanking the first chamber, the second chamber configured to receive particulate waste and serve as a storage component.

24. The waste collection system of claim 22, wherein the first containment layer further comprises a plurality of surfaces sloping toward the at least one aperture.

25. The waste collection system of claim 22, wherein the first containment layer includes a plurality of channels formed between a plurality of surfaces sloping toward the at least one aperture, the plurality of channels configured to deliver the fluids to the at least one aperture.

26. The waste collection system of claim 22, wherein the at least one aperture includes being one of a circular aperture, funnel-shaped aperture or frusto-conical aperture.

27. The waste collection system of claim 22, further comprising a valve member positioned adjacent the at least one aperture, the valve member configured to accept and retain the fluids below the first containment layer.

28. The waste collection system of claim 27, wherein the valve member comprises a funnel-shaped member or a circular disc.

29. The waste collection system of claim 27, wherein the valve member comprises at least one of foam, rubber and plastic.

30. The waste collection system of claim 27, wherein the valve member includes a plurality of flaps extending from the first containment layer, the plurality of flaps surrounding a central opening.

31. The waste collection system of claim 22, wherein the first containment layer comprises:
   a plurality of channels formed between a plurality of sloping surfaces;
   a ledge surrounding the at least one aperture and between each channel of the plurality of channels; and
   a valve member positioned on the ledge such that fluids in the plurality of channels may enter the at least one aperture beneath the valve member.

32. The waste collection system of claim 22, further comprising a second containment layer configured to engage the at least one chamber and the first containment layer.

33. The waste collection system of claim 32, wherein the second containment layer further includes a nook configured to accept a basin of a second waste collection system.

34. The waste collection system of claim 32, wherein the second containment layer is further configured to stabilize the basin.

35. The waste collection system of claim 22, further comprising at least one absorbent layer within the at least one chamber.

36. The waste collection system of claim 35, wherein the at least one absorbent layer includes at least one of wood pulp filler, super-absorbent polymer filler, and a water-based guar gel.

37. The waste collection system of claim 22, further comprising a second vent comprising an S-shaped or L-shaped recess in a portion of the first containment layer.

38. The waste collection system of claim 22, wherein the first containment layer engages the basin through a snap ring, grooves, or a sealing film.

39. The waste collection system of claim 22, further comprising a second containment layer configured to alternately stabilize and cover the basin, wherein the basin includes a plurality of sidewalls, and at least one sidewall of the plurality of sidewalls includes at least one detent and wherein the second containment layer includes at least one pocket for accepting the at least one detent.

40. The waste collection system of claim 22, wherein the first containment layer further includes a hood partially covering the at least one aperture.

41. The waste collection system of claim 22, wherein the first containment layer and the basin are formed of a unitary plastic member.

42. A method of collecting waste including fluid waste, the method comprising:
   providing a receptacle comprising at least one chamber configured to accept the fluid waste and comprising a base and at least one sidewall extending from the base to a top edge, a first sidewall of the at least one sidewall including a recess at the top edge and at least one containment layer at least partially engaging the top edge of the at least one chamber;
   delivering the fluid waste to the receptacle; and
   allowing the recess to release gases from the receptacle.

43. The method according to claim 42, wherein delivering comprises introducing the fluid waste to a surface of the at least one containment layer and allowing the fluid waste to flow into an aperture within the at least one containment layer.

44. The method according to claim 43, wherein allowing the fluid waste to flow into an aperture comprises allowing the fluid waste to flow between the surface and a valve member positioned adjacent the aperture.

45. The method according to claim 42, wherein delivering comprises introducing the fluid waste into an aperture in the at least one containment layer.

46. The method according to claim 42, wherein delivering comprises penetrating a valve member positioned adjacent an aperture in the at least one containment layer.

47. The method according to claim 42, further comprising attaching the receptacle and the at least one containment layer so as to stabilize the receptacle while delivering the fluid waste.

48. The method according to claim 47, further comprising detaching the receptacle and the at least one containment layer and reattaching the receptacle and the at least one containment layer so as to cover the receptacle.

49. The method according to claim 48, further comprising placing a chamber of a second receptacle on the at least one containment layer.

50. The method according to claim 49, further comprising providing at least one absorbent layer within the at least one chamber.

51. The method according to claim 42, wherein allowing the recess to release gases further comprises providing a recess in a portion of the at least one containment layer.

52. The method according to claim 51, wherein allowing the recess to release gases further comprises providing an S-shaped or L-shaped recess in a portion of the at least one containment layer.

53. A lid for use in a waste collection system, the lid comprising:

a plurality of surfaces sloping toward at least one aperture therein;

at least one channel formed between the plurality of sloping surfaces such that a raised ledge is formed between each channel of the at least one channel and each surface of the plurality of surfaces; and a valve member positioned adjacent the at least one aperture proximate the raised ledge such that a gap is formed beneath the valve member and above the at least one channel.

54. The lid of claim 53, wherein the at least one channel is configured to deliver fluid to the at least one aperture.

55. The lid of claim 53, wherein the at least one channel is configured to deliver fluid through the gap and into the at least one aperture.

56. The lid of claim 53, wherein the lid is transparent.

57. The lid of claim 53, wherein the at least one aperture includes one of a circular aperture, funnel-shaped aperture or frusto-conical aperture.

58. The lid of claim 53, wherein the lid is placed on an open-topped receptacle comprising at least one chamber configured to receive fluid.

59. The lid of claim 53, wherein the valve member is configured to accept and substantially retain waste below the lid.

60. The lid of claim 53, wherein the valve member comprises a funnel-shaped member of a circular disc.

61. The lid of claim 53, wherein the valve member comprises a plurality of flaps flanking the at least one aperture and surrounding a central opening within the at least one aperture.

62. The lid of claim 53, further comprising a ledge surrounding the at least one aperture and between the at least one channel, wherein the valve member is positioned on the ledge.

63. The lid of claim 53, further including a vent.

64. The lid of claim 63, wherein the vent comprises an S-shaped or L-shaped recess in at least a portion of the lid.

65. The lid of claim 53, wherein the lid is formed as a unitary member with a receptacle comprising at least one chamber configured to receive fluid.

66. The lid of claim 53, further comprising a snap ring around the perimeter of the lid.

67. The lid of claim 66, wherein the lid is placed on an open-topped receptacle comprising at least one chamber configured to receive fluid.

68. The lid of claim 67, further comprising at least one absorbent layer within the at least one chamber.

69. The lid of claim 68, further comprising a containment layer covering the lid and the receptacle.

70. The lid of claim 53, further comprising a stop within the at least one aperture configured to prevent a fluid delivery device from penetrating the at least one aperture below a predetermined distance.

* * * * *

UNITED STATES PATENT AND TRADEMARK OFFICE
CERTIFICATE OF CORRECTION

PATENT NO. : 6,719,017 B1
DATED : April 13, 2004
INVENTOR(S) : Greg McArthur, Fred P. Lampropoulos and Arlin D. Nelson It is certified that error appears in the above-identified patent and that said Letters Patent is hereby corrected as shown below:

Title page,
Item [57], ABSTRACT,
Line 6, at the end of the line, after "the" insert -- at least one --

Column 18,
Line 31, before "perimeter" change "the" to -- a --

Signed and Sealed this

Twenty-fifth Day of January, 2005

JON W. DUDAS
*Director of the United States Patent and Trademark Office*